US012667673B2

(12) United States Patent
Maxfield

(10) Patent No.: US 12,667,673 B2
(45) Date of Patent: Jun. 30, 2026

(54) CAP ASSEMBLY FOR A MEDICAMENT DELIVERY DEVICE

(71) Applicant: SHL MEDICAL AG, Zug (CH)

(72) Inventor: Brian Maxfield, Delray Beach, FL (US)

(73) Assignee: SHL Medical AG, Zug (CH)

( * ) Notice: Subject to any disclaimer, the term of this patent is extended or adjusted under 35 U.S.C. 154(b) by 805 days.

(21) Appl. No.: 17/233,190

(22) Filed: Apr. 16, 2021

(65) Prior Publication Data

US 2021/0228814 A1     Jul. 29, 2021

Related U.S. Application Data

(63) Continuation of application No. 16/232,852, filed on Dec. 26, 2018, now Pat. No. 10,980,949, which is a
(Continued)

(51) Int. Cl.
*A61M 5/32*          (2006.01)
*A61M 5/24*          (2006.01)

(52) U.S. Cl.
CPC ... *A61M 5/3204* (2013.01); *A61M 2005/2407* (2013.01); *A61M 2005/244* (2013.01); *A61M 5/3213* (2013.01); *A61M 2207/00* (2013.01)

(58) Field of Classification Search
CPC .............. A61M 5/3205; A61M 5/3213; A61M 2005/244; A61M 5/3202; A61M 5/3204;
(Continued)

(56) References Cited

U.S. PATENT DOCUMENTS 5,928,205 A * 7/1999 Marshall ................. A61M 5/24
                                                    604/232
2004/0199117 A1    10/2004  Giambattista et al.
(Continued)

FOREIGN PATENT DOCUMENTS

CN          1777453 A      5/2006
CN       103550848 A      2/2014
(Continued)

OTHER PUBLICATIONS

International Search Report issued in International Application No. PCT/EP2018/061043 dated Jul. 25, 2018.

*Primary Examiner* — Kevin C Sirmons
*Assistant Examiner* — Leah J Swanson
(74) *Attorney, Agent, or Firm* — McDonnell Boehnen Hulbert & Berghoff LLP

(57)          ABSTRACT

A cap assembly for a medicament delivery device is disclosed. The cap assembly includes a cap configured to be mounted to a proximal end of the medicament delivery device, wherein the cap comprises a cam surface. The cap assembly further includes a squeezer comprising (i) a body defining a first longitudinally extending channel configured to receive a delivery member shield and (ii) a plurality of radial arms flexible in a radial direction. The cap assembly also includes a spinner comprising (i) a proximal end face configured to cooperate with the cam surface of the cap, (ii) a body defining a second longitudinally extending channel configured to receive the squeezer, and (iii) a plurality of holes in the body of the spinner configured to receive the plurality of radial arms of the squeezer.

17 Claims, 16 Drawing Sheets

Related U.S. Application Data continuation of application No. 15/583,467, filed on May 1, 2017, now Pat. No. 10,307,545.

(58) Field of Classification Search
CPC .. A61M 2005/3215; A61M 2005/2437; A61M 2005/2403; A61M 2005/2407; A61M 2005/2433; A61M 5/24; A61M 2005/3117; A61M 2207/00
See application file for complete search history.

(56) References Cited

U.S. PATENT DOCUMENTS

| | | | | |
|---|---|---|---|---|
| 2012/0203186 A1* | 8/2012 | Vogt | ............... | A61M 5/3204 |
| | | | | 604/192 |
| 2014/0343503 A1* | 11/2014 | Holmqvist | .......... | A61M 5/3204 |
| | | | | 81/3.4 |
| 2018/0028762 A1 | 2/2018 | Maxfield | | |

FOREIGN PATENT DOCUMENTS

| | | | |
|---|---|---|---|
| GB | 2541915 | A | 3/2017 |
| TW | 201336538 | A | 9/2013 |
| TW | 201404420 | A | 2/2014 |
| WO | 2014009705 | A1 | 1/2014 |
| WO | 2015/110533 | A2 | 7/2015 |
| WO | 2015110532 | A1 | 7/2015 |
| WO | 2016159782 | A2 | 10/2016 |
| WO | 2016/193356 | A1 | 12/2016 |
| WO | 2017/037469 | A1 | 3/2017 |

* cited by examiner

| Providing medicament container assembly | —A |
| Moving clamp member over delivery member shield | —B |
| Moving clamp member in distal direction | —C |

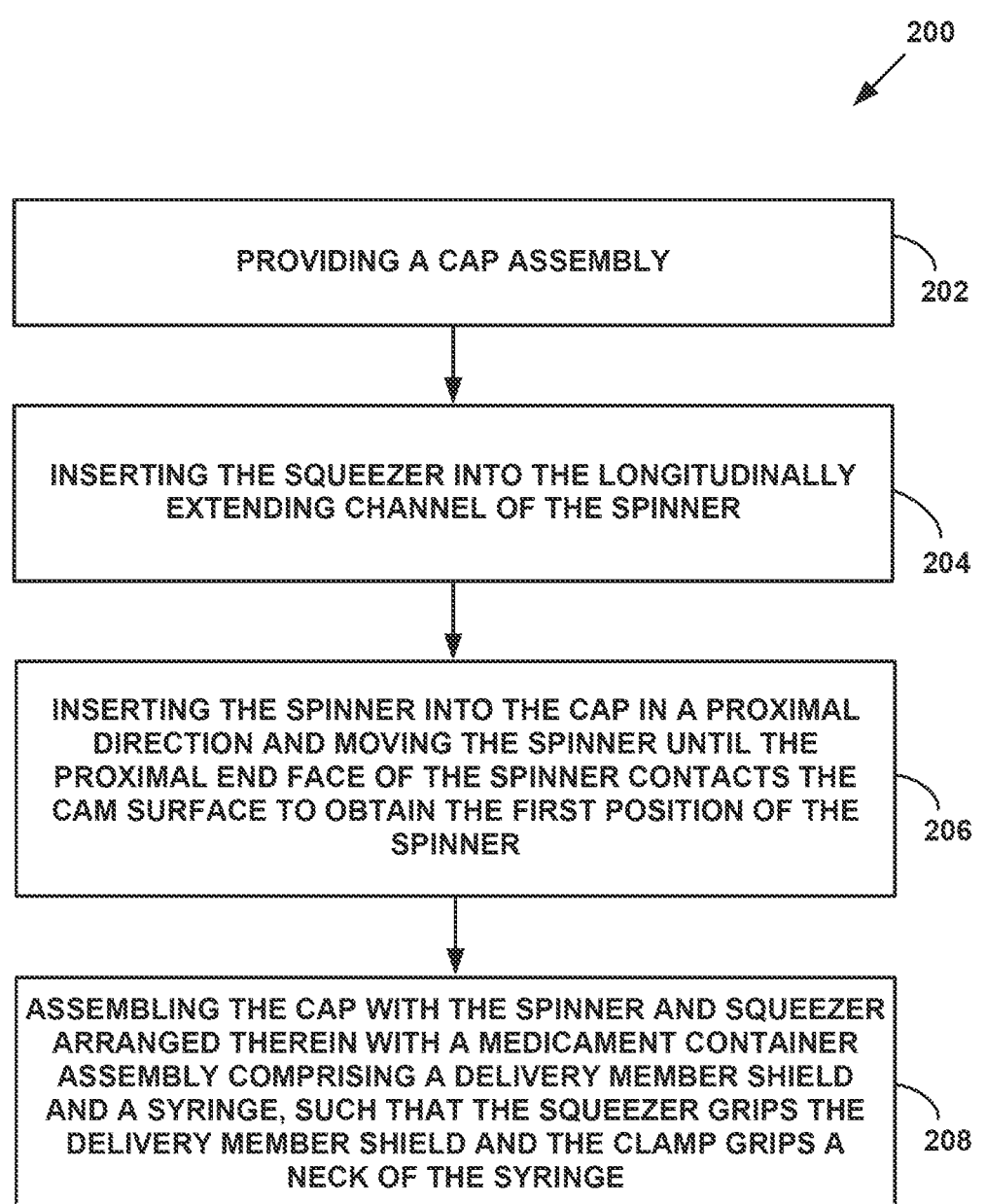

200

PROVIDING A CAP ASSEMBLY    202

INSERTING THE SQUEEZER INTO THE LONGITUDINALLY EXTENDING CHANNEL OF THE SPINNER    204

INSERTING THE SPINNER INTO THE CAP IN A PROXIMAL DIRECTION AND MOVING THE SPINNER UNTIL THE PROXIMAL END FACE OF THE SPINNER CONTACTS THE CAM SURFACE TO OBTAIN THE FIRST POSITION OF THE SPINNER    206

ASSEMBLING THE CAP WITH THE SPINNER AND SQUEEZER ARRANGED THEREIN WITH A MEDICAMENT CONTAINER ASSEMBLY COMPRISING A DELIVERY MEMBER SHIELD AND A SYRINGE, SUCH THAT THE SQUEEZER GRIPS THE DELIVERY MEMBER SHIELD AND THE CLAMP GRIPS A NECK OF THE SYRINGE    208

FIG. 29

CAP ASSEMBLY FOR A MEDICAMENT DELIVERY DEVICE

CROSS REFERENCE TO RELATED APPLICATIONS

The present application is a continuation of U.S. application Ser. No. 16/232,852, filed Dec. 26, 2018, now U.S. Pat. No. 10,980,949, which is a continuation of U.S. Application No. 15/583,467 filed May 1, 2017, now U.S. Pat. No. 10,307,545. The entire disclosure contents of these applications are herewith incorporated by reference into the present application.

TECHNICAL FIELD

The present disclosure generally relates to medical devices. In particular, it relates to a cap assembly for a medicament delivery device, to a medicament delivery device comprising such a cap assembly, and to a method of assembling a sub-assembly for a medicament delivery device.

BACKGROUND

Medicament delivery devices, such as injectors and inhalers, typically comprise a housing in which a medicament container containing a medicament is to be arranged. Upon activation of the medicament delivery device, the medicament is expelled through a medicament delivery member, for example a needle or a nozzle.

In order to protect and to keep the medicament delivery member sterile, the medicament delivery member may be provided with a delivery member shield, or sheath, such as a Flexible Needle Shield (FNS) or a Rigid Needle Shield (RNS). The delivery member shield may thus be attached to the medicament container to cover the medicament delivery member, during assembly of the medicament container or of the medicament delivery device.

Moreover, the medicament delivery device may comprise a removable cap which is mounted to the proximal end of the housing, i.e. that end which is placed towards the injection site during medicament delivery, of the medicament delivery device, or to the proximal end of the medicament container. The removable cap has the function of providing mechanical protection of the medicament delivery member while attached to the housing or medicament container, and to remove the delivery member shield when the cap is removed from the housing.

WO2015110532 A1 discloses an auto-injector having a connector for connecting a needle cover to a removable cap. The connector has a plurality of legs spaced symmetrically away from one another about a central hub. The legs have an elastic nature and aid in securing the needle cover and/or rigid needle shield to a cap insert and hence to the removable cap. The needle cover and/or needle shield are secured together through upper, internally facing barbs protruding from the first legs. The upper, internally facing barbs include tips that point toward the forward end of the connector. These barbs are shaped to engage the needle cover and/or rigid needle shield when the needle cover and/or rigid needle shield is fitted within the connector. The barb tips apply opposing force with respect to one another when they engage the needle cover and/or rigid needle shield when the needle cover and/or rigid needle shield is fitted within the connector.

SUMMARY

According to the design disclosed in WO2015110532 A1, the legs of the connector are flexed towards each other as soon as the connector is placed in the cap insert. This bending of the legs renders it more difficult to insert the needle cover/rigid needle shield into the connector, thereby making assembly more difficult.

In view of the above, a general object of the present disclosure is to provide a cap assembly for a medicament delivery device which solves or at least mitigates the problems of the prior art.

There is hence according to a first aspect of the present disclosure provided a cap assembly for a medicament delivery device, comprising: a cap having a tubular body defining an axially extending distal opening and configured to be mounted to a proximal end of a medicament delivery device, wherein the cap has a bottom structure defining a proximal end of the distal opening, wherein the bottom structure has a cam structure provided inside the tubular body, and wherein the tubular body has inner walls provided with radial recesses extending in the longitudinal direction along the inner walls, and an elongated squeeze member configured to be received in the distal opening of the tubular body, and having a longitudinally extending channel configured to receive a delivery member shield, and which squeeze member has radial arms flexible in the radial direction and forming part of a wall of the channel, wherein the squeeze member has a proximal end face configured to cooperate with the cam structure of the cap, whereby axial displacement of the squeeze member from a first position in which the proximal end face bears against the cam structure to a second position in which the squeeze member is received further by the cap causes rotation of the squeeze member relative to the cap, wherein the radial arms are configured to engage with a respective radial recess of the tubular body in the first position of the squeeze member, and wherein the radial arms are configured to disengage from the respective radial recess when the squeeze member is displaced from the first position to the second position and rotated, whereby the flexible radial arms are pressed into the channel by the inner walls of the tubular body, reducing a cross-sectional area of the channel.

The squeeze member is thus able to provide radial pressure on, or squeeze, a delivery member shield when a delivery member shield is inserted into the channel of the squeeze member and the squeeze member is moved proximally inside the distal opening of the cap, to the second position. The cap may hence in a simple manner be mounted to the delivery member shield, and removed from a medicament container when the cap assembly is removed from a medicament delivery device.

According to one embodiment the cam structure is annular in a radial plane and comprises a plurality of elevated portions with a cut-out having oppositely inclined surfaces provided between each adjacent pair of elevated portions, in the circumferential direction of the cam structure.

According to one embodiment the proximal end face of the squeeze member comprises a plurality of elevated portion with a cut-out having oppositely inclined surfaces provided between each adjacent pair of elevated portions of the proximal end face, in the circumferential direction of the squeeze member.

According to one embodiment each elevated portion of the squeeze member is configured to bear against a region of a cut-out of the cam structure closer to an elevated portion of the cam structure than to a lowest elevational point of the cut-out, in the first position of the squeeze member.

According to one embodiment the elevated portions of the squeeze member are configured to engage with the cut-outs of the cam structure in the second position of the squeeze member.

According to one embodiment at least two of the radial arms are arranged opposite to each other in a radial plane of the squeeze member, causing the two radial arms to move towards each other in the second position of the squeeze member.

According to one embodiment two of the radial arms are arranged in a first radial plane of the squeeze member, and wherein two other radial arms are arranged in a second radial plane axially spaced apart from the first radial plane.

According to one embodiment the two radial arms arranged in the first plane are arranged 90 degrees offset in the circumferential direction relative to the two arms arranged in the second plane.

According to one embodiment the radial recesses have inclined surfaces in the circumferential direction allowing the radial arms to disengage when the squeeze member is rotated while displaced from the first position to the second position.

According to one embodiment the radial arms have an increasing thickness in a direction from their point of attachment towards their end portions, wherein the thickness of each end portion is thicker than a wall thickness of the channel.

According to one embodiment the radial recesses extend in the longitudinal direction along a majority of the length of the inner walls of the tubular body.

There is according to a second aspect of the present disclosure provided a medicament delivery device comprising: a body having a proximal opening, and a cap assembly according to the first aspect, wherein the cap assembly is configured to be mounted to the medicament delivery device to cover the proximal opening of the body.

One embodiment comprises a surface configured to bear against a distal end face of the squeeze member.

There is according to a third aspect provided a method of assembling a sub-assembly for a medicament delivery device, comprising: a) providing a cap assembly according to the first aspect, b) inserting the squeeze member into the distal opening of the cap and moving the squeeze member towards the bottom structure until the proximal end face of the squeeze member contacts the cam structure to obtain the first position of the squeeze member, and c) assembling the cap with the squeeze member arranged therein with a medicament container assembly comprising a delivery member shield, such that the squeeze member receives the delivery member shield.

According to one embodiment step c) includes moving a distal end face of the squeeze member towards a proximal surface of the medicament container assembly, causing the squeeze member to move proximally inside the cap from the first position to the second position causing the radial arms to squeeze the delivery member shield.

According to one embodiment the delivery member shield is a rigid needle shield or a flexible needle shield.

There is according a fourth aspect of the present disclosure a cap assembly for a medicament delivery device. In an example embodiment of this aspect, the cap assembly includes a cap configured to be mounted to a proximal end of the medicament delivery device, wherein the cap comprises a cam surface. The cap assembly further includes a squeezer comprising (i) a body defining a first longitudinally extending channel configured to receive a delivery member shield and (ii) a plurality of radial arms flexible in a radial direction. Still further, the cap assembly includes a spinner comprising (i) a proximal end face configured to cooperate with the cam surface of the cap, (ii) a body defining a second longitudinally extending channel configured to receive the squeezer, and (iii) a plurality of holes in the body of the spinner configured to receive the plurality of radial arms of the squeezer. Axial displacement of the spinner from (i) a first position in which the proximal end face bears against the cam surface and each radial arm of the plurality of radial arms is positioned in a respective hole of the plurality of holes to (ii) a second position in which the spinner is received further by the cap causes rotation of the spinner relative to the cap and the squeezer. Further, rotation of the spinner relative to the cap and the squeezer causes the body of the spinner to force each radial arm out of the respective hole and into the first longitudinally extending channel, so as to reduce a cross-sectional area of the first longitudinally extending channel.

There is according a fifth aspect of the present disclosure a medicament delivery device. In an example embodiment of this aspect, the medicament delivery device includes a body having a proximal opening and a cap assembly such as the cap assembly according to the fourth aspect. The cap assembly is configured to be mounted to the medicament delivery device to cover the proximal opening of the body.

There is according a sixth aspect of the present disclosure a cap assembly for a medicament delivery device. In an example embodiment of this aspect, the cap assembly includes a cap configured to be mounted to a proximal end of the medicament delivery device, wherein the cap comprises a cam surface. The cap assembly further includes a squeezer comprising (i) a body defining a first longitudinally extending channel configured to receive a delivery member shield and (ii) a plurality of radial arms flexible in a radial direction. Still further, the cap assembly includes a spinner comprising (i) a proximal end face configured to cooperate with the cam surface of the cap, (ii) a body defining a second longitudinally extending channel configured to receive the squeezer, and (iii) a plurality of holes in the body of the spinner configured to receive the plurality of radial arms of the squeezer. Yet still further, the cap assembly includes a clamp axially fixed to a distal end of the squeezer, wherein the clamp comprises a plurality of clamp arms flexible in a radial direction from an open position to a closed position. Axial displacement of the spinner from (i) a first position in which the proximal end face bears against the cam surface and each radial arm of the plurality of radial arms is positioned in a respective hole of the plurality of holes to (ii) a second position in which the spinner is received further by the cap causes rotation of the spinner relative to the cap and the squeezer. Rotation of the spinner relative to the cap and the squeezer causes the body of the spinner to force each radial arm out of the respective hole and into the first longitudinally extending channel, so as to reduce a cross-sectional area of the first longitudinally extending channel.

There is according a seventh aspect of the present disclosure a method of assembling a sub-assembly for a medicament delivery device. In an example embodiment of this aspect, the method includes providing a cap assembly such as the cap assembly of the sixth aspect. The method further includes inserting the squeezer into the second longitudinally extending channel of the spinner and inserting the spinner into the cap in a proximal direction and moving the spinner until the proximal end face of the spinner contacts the cam surface to obtain the first position of the spinner.

Still further, the method includes assembling the cap with the spinner and squeezer arranged therein with a medicament container assembly comprising a delivery member shield and a syringe, such that the squeezer grips the delivery member shield and the clamp grips a neck of the syringe.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE FIGURES

The specific embodiments of the inventive concept will now be described, by way of example, with reference to the accompanying drawings, in which:

FIG. 29 illustrates an example method, according to an example embodiment of the present disclosure.

DETAILED DESCRIPTION

Figures 1, 2:
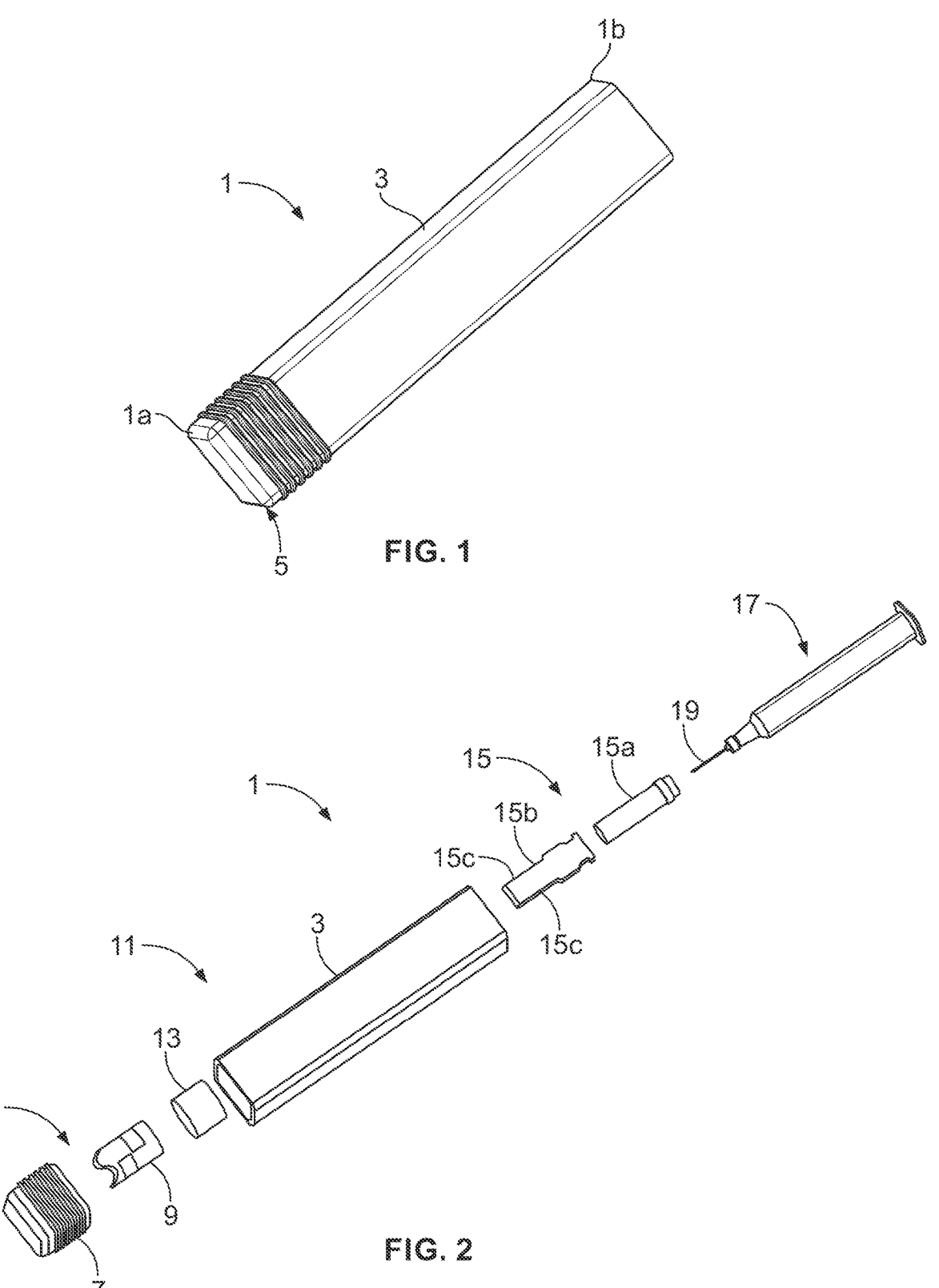
FIG. 1 is a perspective view of an example of a medicament delivery device without an activation assembly.
FIG. 2 shows an exploded view of the medicament delivery device in FIG. 1.

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The term "proximal end" as used herein, when used in conjunction with a cap assembly, refers to that end of the cap assembly which is farthest from the proximal end of the medicament delivery device, when the cap assembly is properly mounted onto a medicament delivery device. The proximal end of a medicament delivery device is that end which is to be pointed towards the injection site during medicament injection. The same considerations also apply when referring to any component of the cap assembly. The "distal end" is the opposite end relative to the proximal end. With "proximal direction" and, equivalently, "proximally" is meant a direction from the distal end towards the proximal end, along the central axis of the safety mechanism. With "distal direction" or "distally" is meant the opposite direction to "proximal direction". The same definition also applies for the medicament container and any component thereof.

The present disclosure relates to a cap assembly for a medicament delivery device. The cap assembly includes a cap and an elongated squeeze member. The cap is configured to be mounted to a proximal end of a medicament delivery device, for example to the housing, or body, of a medicament delivery device. The cap has a tubular body which has a distal opening extending along the central axis of the tubular body.

The tubular body has a bottom structure which defines the proximal end wall of the distal opening. The bottom structure has a cam structure, provided inside the tubular body, in particular inside the distal opening. The tubular body has inner walls, i.e. the inner walls of the distal opening provided with radial recesses.

The squeeze member is configured to be received by the tubular body, in particular in the distal opening. The squeeze member has a longitudinally extending channel configured to receive a delivery member shield. The squeeze member furthermore has radial arms that are flexible in the radial direction. The radial arms form part of a channel wall(s). The squeeze member furthermore has a proximal end face configured to cooperate with the cam structure of the cap. The squeeze member is configured to be axially displaceable from a first position in which the proximal end face bears against the cam structure to a second position in which the squeeze member is received further by the cap. This axial displacement causes rotation of the squeeze member relative to the cap, and is obtained due to the cooperating proximal end face of the squeeze member and the cam structure of the cap.

The radial arms extend radially outside the outer surface of the squeeze member when the squeeze member is arranged in the first position. In the first position, each radial arm is received by a respective radial recess of the tubular body. When the squeeze member is rotated, the radial arms disengage from the radial recesses, and as the squeeze member rotates so that the radial arms are moved in the circumferential direction away from their respective radial recess, the radial arms are pressed radially inwards by the inner walls of the tubular body. This causes the radial arms to extend radially inwards of the inner surface of the channel of the squeeze member, reducing a cross-sectional area of the channel. The radial arms may thereby provide radial pressure onto a delivery member shield received by the squeeze member. The cap assembly can thus engage with the delivery member shield such that when the cap assembly is removed from a medicament delivery device, the delivery member shield is removed simultaneously.

With reference to FIGS. 1-10 an example of a cap assembly will be described.

FIG. 1 shows a perspective view of a medicament delivery device 1, which in the present case may also be seen as a sub-assembly of a medicament delivery device, because the depicted example does not comprise an activation assembly, which is to be mounted to a distal end of the medicament delivery device 1.

The exemplified medicament delivery device 1 shown in FIG. 1 has a proximal end 1a and a distal end 1b, and comprises a body, or housing, 3, and a cap assembly 5.

Turning now to FIG. 2, an exploded view of the medicament delivery device 1 is shown. The medicament delivery device 1 comprises the cap assembly 5, which comprises a cap 7 and a squeeze member 9, a medicament container assembly 11, which comprises the body 3 and a clamp member 13. The medicament delivery device 1 may further include a delivery member shield 15 and a medicament container 17 including a delivery member 19.

According to the example shown in FIG. 2, the medicament container 17 is a syringe and the delivery member 19 is a needle. Moreover, the exemplified the delivery member shield 15 includes a flexible inner member 15a configured to receive the delivery member 19 and a rigid outer member 15b configured to receive the flexible inner member 15a. The rigid outer member 15b has chamfered outer surfaces 15c extending parallel with each other in the longitudinal direction of the delivery member shield 15. The exemplified delivery member shield 15 is a rigid needle shield, but could alternatively be a flexible needle shield.

Figure 3:
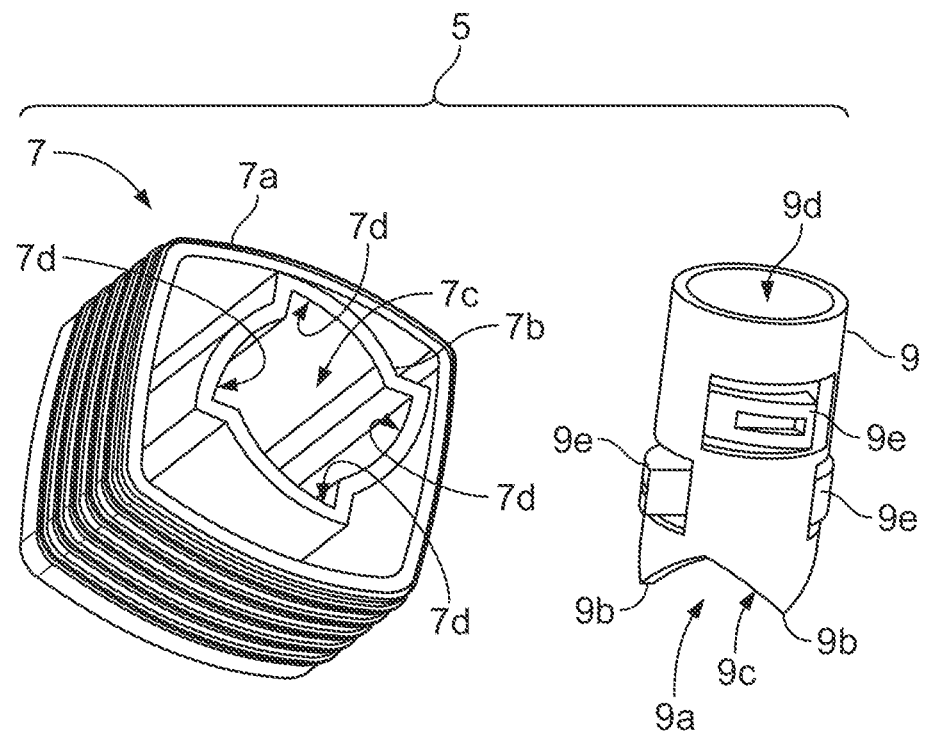
FIG. 3 shows an example of a cap assembly.

FIG. 3 shows a detailed view of the cap assembly 5. The exemplified cap 7 has an outer body 7a and an inner tubular body 7b, coaxially arranged with the outer body. The tubular body 7b has an axially extending distal opening 7c. The tubular body 7b is configured to receive the squeeze member 9 in the distal opening 7c.

The tubular body 7b has a plurality of radial recesses 7d. The radial recesses 7d extend in the longitudinal direction along a majority of the axial length of the tubular body 7b, and thus of the distal opening 7c.

The squeeze member 9 is elongated and has a tubular shape. The squeeze member 9 has a channel 9d extending in the longitudinal direction through the squeeze member 9, configured to receive the delivery member shield 15.

The squeeze member 9 furthermore has a proximal end face 9a comprising a plurality of elevated portions 9b. Between each pair of adjacent pair of elevated portions 9b is a cut-out 9c with oppositely inclined or sloping surfaces. The proximal end face 9a is hence provided with a plurality of teeth in the circumferential direction of the squeeze member 9, with a gradually increasing and decreasing elevation.

The squeeze member 9 comprises a plurality of radial arms 9e which are flexible in the radial direction. The radial arms 9e extend the circumferential direction from the main body of the squeeze member 9 and have an increasing thickness towards their end portions relative to the point of attachment to the main body of the squeeze member 9. Hereto, the end thickness of each radial arm is substantially thicker than the thickness of the channel wall.

The radial arms 9e form part of the channel wall. The radial arms 9e are by default configured to flex radially outwards from the outer surface of the squeeze member 9, as shown in FIG. 3. Hereto, the radial arms 9e protrude radially from the outer surface of the main body of the squeeze member 9 when no external force is applied to the radial arms 9e. The radial arms 9e are configured to slide axially in a respective radial recess 7d of the cap 7, when the squeeze member 9 is moved linearly in the distal opening 7c of the tubular body 7b. The radial recess 7d have inclined surfaces in the circumferential direction, allowing the radial arms 9e to disengage from the radial recesses 7d when the squeeze member 9 is rotated while being displaced in the distal opening 7c, from a first position to a second position. The radial recesses 7d and the radial arms 9e may be seen to form a ratchet configuration, with the radial arms 9e being flexible radially inwards when the squeeze member 9 disengage from the radial recesses 7d and the squeeze member 9 is being rotated.

According to the example shown in FIG. 3, the squeeze member 9 has a plurality of arms 9e in a first radial plane along the axial direction of the squeeze member 9, and a plurality of radial arms 9e in a second plane axially spaced apart from the first plane. The exemplified squeeze member 9 hence has several layers of radial arms 9e, in the axial direction of the squeeze member 9.

Figure 4:
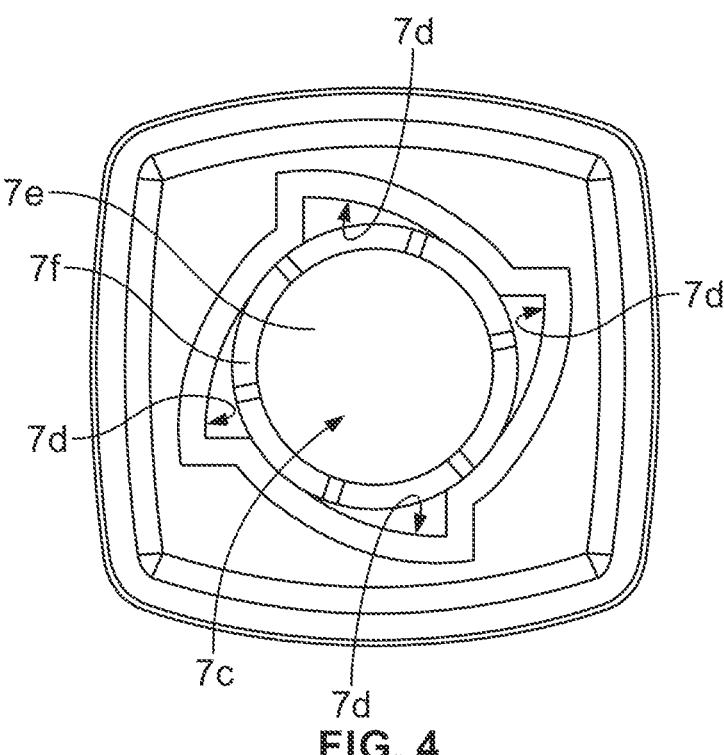
FIG. 4 is a top view of a cap.

FIG. 4 shows a top view of the cap 7, in particular seen from the distal end of the cap 7. The cap 7 has a bottom structure 7e, which defines a distal end wall or surface of the distal opening 7c. The bottom structure 7e has a cam structure 7f, which according to the present example is annular in a radial plane. The cam structure 7f is configured to cooperate with the proximal end face 9a of the squeeze member 9.

Figure 5:
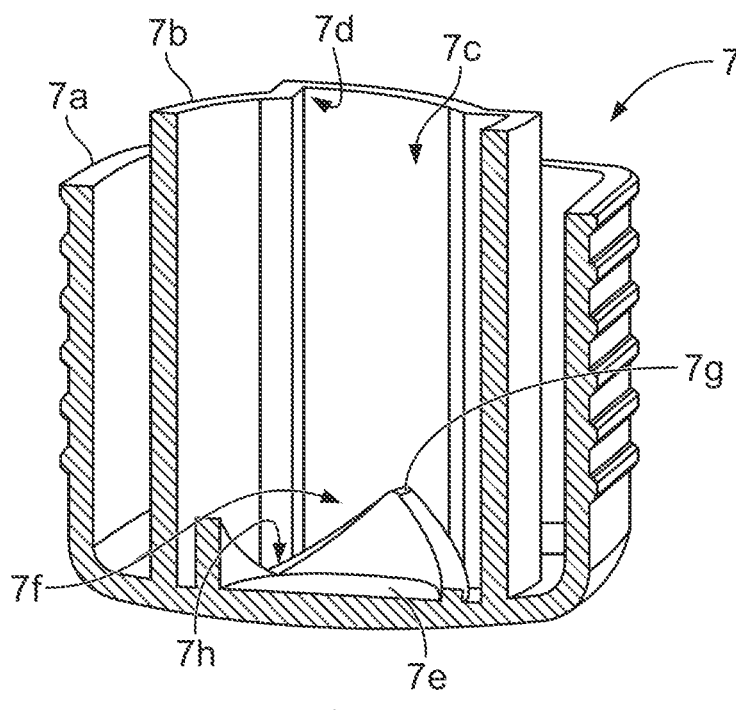
FIG. 5 is a longitudinal section of the cap in FIG. 4.

FIG. 5 shows a longitudinal section of the cap 7. The cam structure 7f has a plurality of slanting surfaces, forming a gradually increasing and decreasing teeth-like structure in the circumferential direction. Hereto, the cam structure 7f has a plurality of elevated portions 7g, of which one can be seen in FIG. 5, and cut-outs 7h with oppositely arranged inclined surfaces. Between each pair of adjacent elevated portion 7g, there is provided a cut-out 7h. This configuration of the cam structure 7f allows for cooperation with the corresponding structure of the proximal end face 9a of the squeeze member 9, as will be described in more detail in the following.

Figure 6:
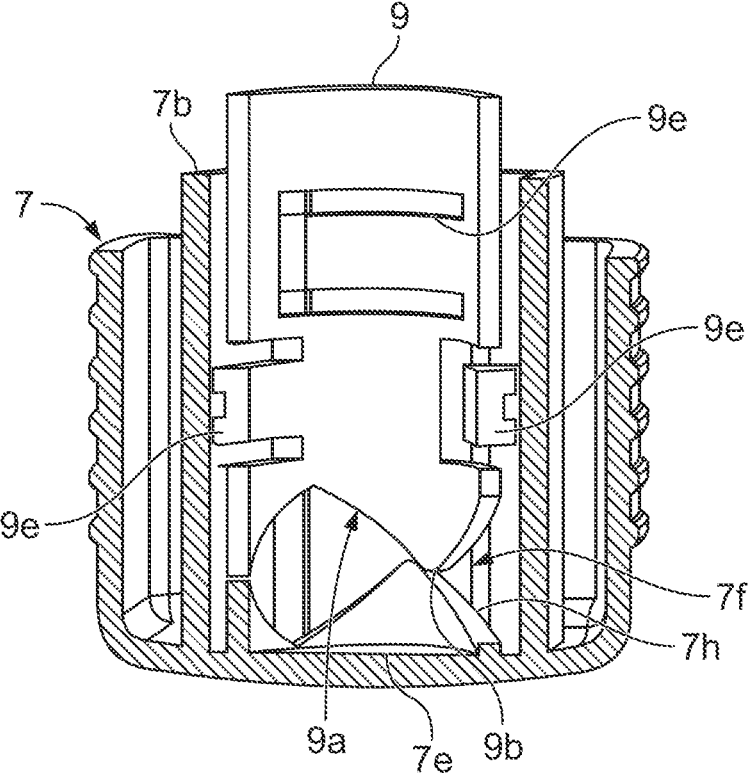
FIG. 6 shows the squeeze member arranged in the cap in a first position of the squeeze member.

FIG. 6 shows the squeeze member 9 arranged inside the tubular body 7b of the cap 7. The squeeze member 9 is arranged in a first position relative to the cap 7. Here, the proximal end face 9a of the squeeze member 9 bears against the cam structure 7f arranged inside the tubular body 7b. Each elevated portion 9b of the squeeze member 9 bears against a respective top portion of the cut-out 7h, closer to an elevated portion of the cam structure 7f than to the lowest elevational point of the cut-out 7h.

Figure 7:
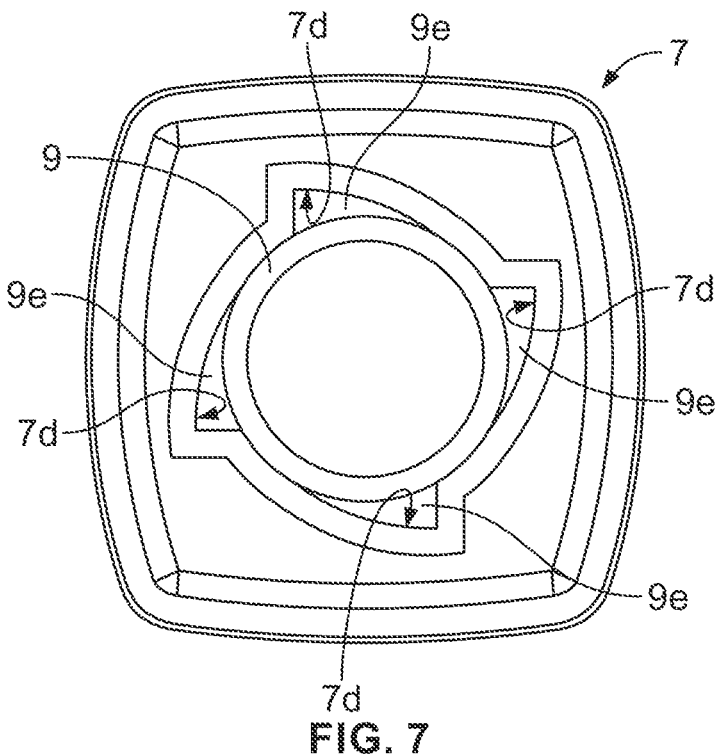
FIG. 7 is a top view of the cap assembly shown in FIG. 6.

As shown in the top view of FIG. 7, each radial arm 9e of the squeeze member 9 is arranged in a respective radial recess 7d of the inner walls of the tubular body 7b when the squeeze member 9 is in the first position.

Figure 8:
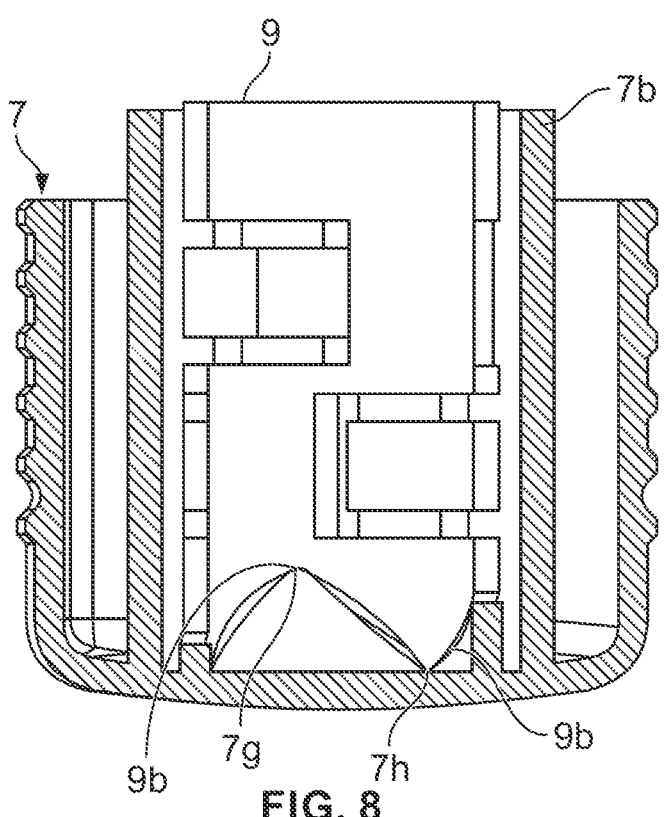
FIG. 8 is a longitudinal section of the squeeze member arranged in the cap in a second position of the squeeze member.

FIG. 8 shows the squeeze member 9 in a second position. In the second position, the squeeze member 9 has been axially displaced relative to the first position shown in FIG. 6. In particular, the squeeze member 9 has been further received by the tubular body 7b. Due to this proximal displacement of the squeeze member 9 the proximal end face 9a and the cam structure 7f have cooperated, causing the squeeze member 9 to rotate relative to the cap 7. Hereto, the elevated portions 9b of the proximal end face 9a have slid down to the lowest elevational points of the cut-outs 7h of the cam structure 7f. Moreover, the elevated portions 7g of the cam structure 7f have been fully received by the cut-out 9c of the proximal end face 9a of the squeeze member 9.

Figure 9:
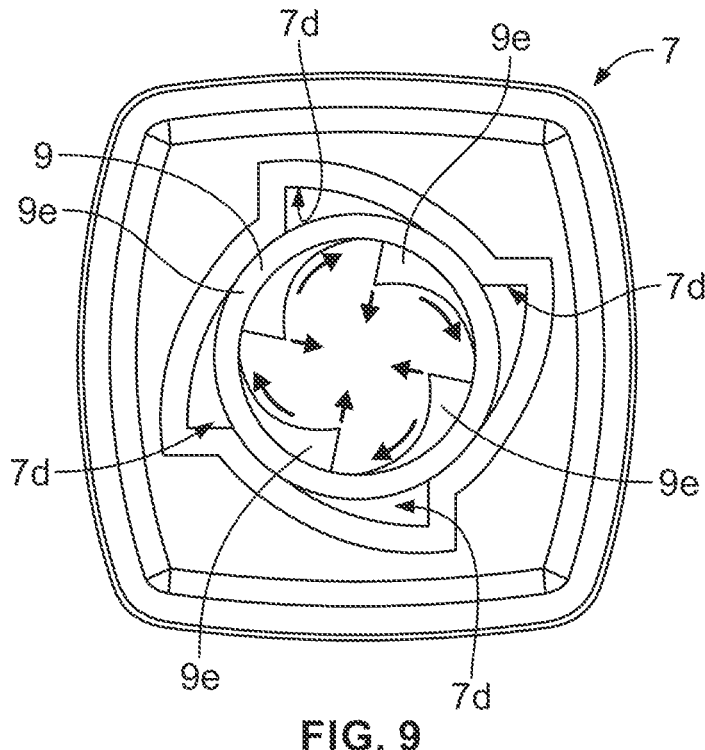
FIG. 9 is a top view of the cap assembly shown in FIG. 8.

In FIG. 9, a top view of the situation shown in FIG. 8 is depicted. The radial arms 9e have disengaged from the radial recesses 7d as the squeeze member 9 is moved proximally from the first position to the second position, causing the squeeze member 9 to rotate, as indicated by the arrows showing rotation. This causes the radial arms 9e to bear against the inner walls of the tubular body 7b, outside the radial recesses 7d, which are radially closer to the central axis of the tubular body 7b. The radial arms 9e are therefore pressed or flexed radially inwards. The radial arms 9e have end portions that are thicker than the wall thickness of the channel 9d, and therefore, the radial arms 9e are pressed into the channel 9d, reducing the cross-sectional area of the channel 9d. When the delivery member shield 15 is arranged in the channel 9d, the radial arms 9e will engage with, or press against, the outer surface of the delivery member shield 15.

Figure 10:
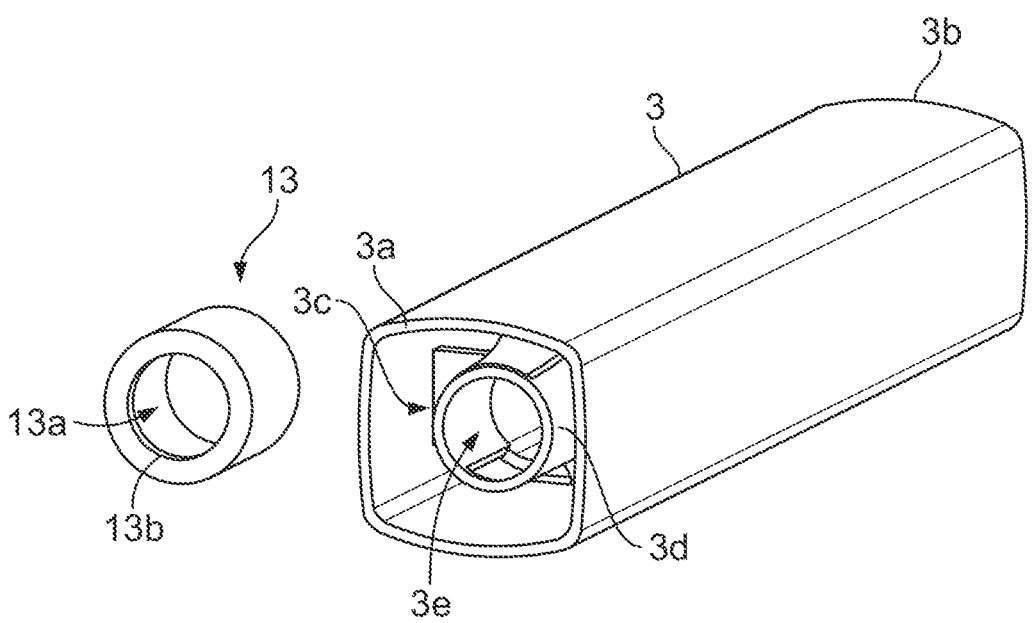
FIG. 10 shows a perspective view of an example of a medicament container assembly.

FIG. 10 shows the medicament container assembly 11. It should be noted that other medicament container assemblies than the one described herebelow may be used in conjunction with the cap assembly 5 previously described. Similarly, the below described medicament container assembly 11 may be used in conjunction with other cap assemblies than the exemplified cap assembly 5.

The exemplified medicament container assembly 11 includes the body 3 and the clamp member 13.

The clamp member 13 is tubular and has a through-opening 13a extending in the longitudinal direction of the clamp member 13. The clamp member 13 furthermore has a proximal end flange 13, or support surface, extending radially inwards.

The body 3 has an elongated shape and is configured to receive the medicament container 17. The body 3 has a proximal end 3a and a distal end 3b and a support structure 3c arranged inside the body 3, closer to the proximal end 3a than to the distal end 3b. The support structure 3c extends between opposite inner surfaces of the body 3. The support structure 3c is provided on, or attached to, the opposite inner surfaces of the body 3. The support structure 3c has a central tubular portion 3d provided with an axially extending through-opening 3e configured to receive the medicament container 17.

Figure 11:
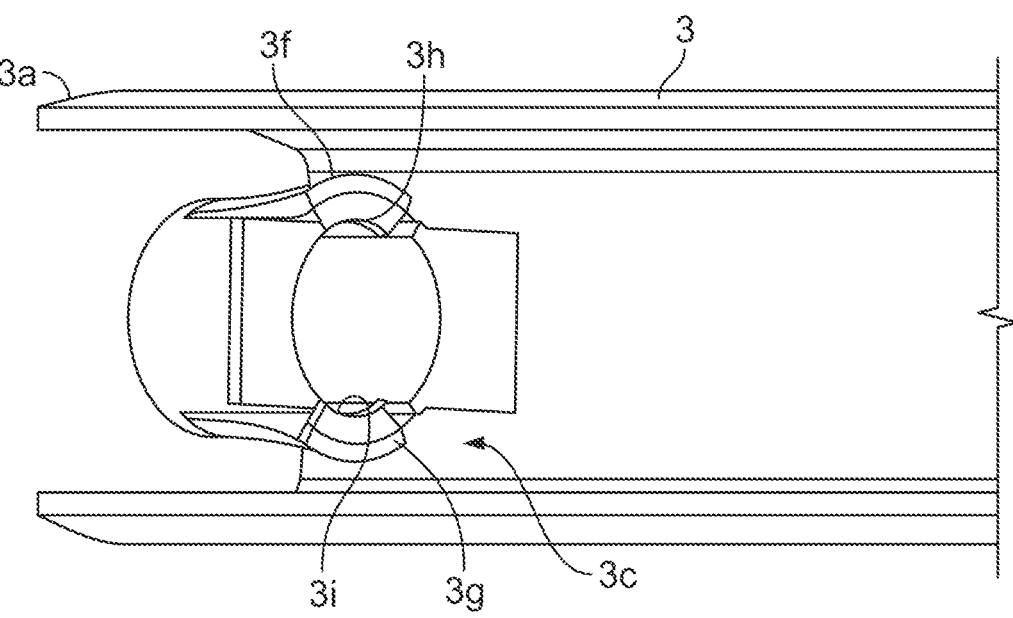
FIG. 11 shows a longitudinal section of a proximal portion of an elongated body of the medicament container assembly.

As shown in FIG. 11, the body 3 furthermore has a radially flexible first gripper arm 3f and a radially flexible second gripper arm 3g arranged opposite relative to the first gripper arm 3f. The first gripper arm 3f and the second gripper arm 3g extend in the axial direction of the body 3.

The first gripper arm 3f and the second gripper arm 3g are configured to support a neck portion of the medicament container 17. According to the example shown in FIG. 11, the first gripper arm 3f and the second gripper arm 3g form part of the tubular portion 3d.

The first gripper arm 3f has a gripper portion 3h provided at a distal end of the first gripper arm 3f, extending radially inwards. The second gripper arm 3g has a gripper portion 3i provided at a distal end of the second gripper arm 3g, extending radially inwards.

The clamp member 13 is configured to receive the tubular portion 3d of the body 3. In particular, the clamp member 13 is configured to be brought around the tubular portion 3d from the proximal end 3a of the body 3, and moved around the tubular portion 3d such that the first gripper arm 3f and the second gripper arm 3g are received by the clamp member 13 and pressed radially inwards by the inner surface of the clamp member 13. When the clamp member 13 has been set in its end position during assembly, the proximal end flange 13b of the clamp member 13 bears against the proximal end of the tubular portion 3d.

With reference to FIGS. 12-15 methods of assembling a sub-assembly will now be described.

Figure 12:
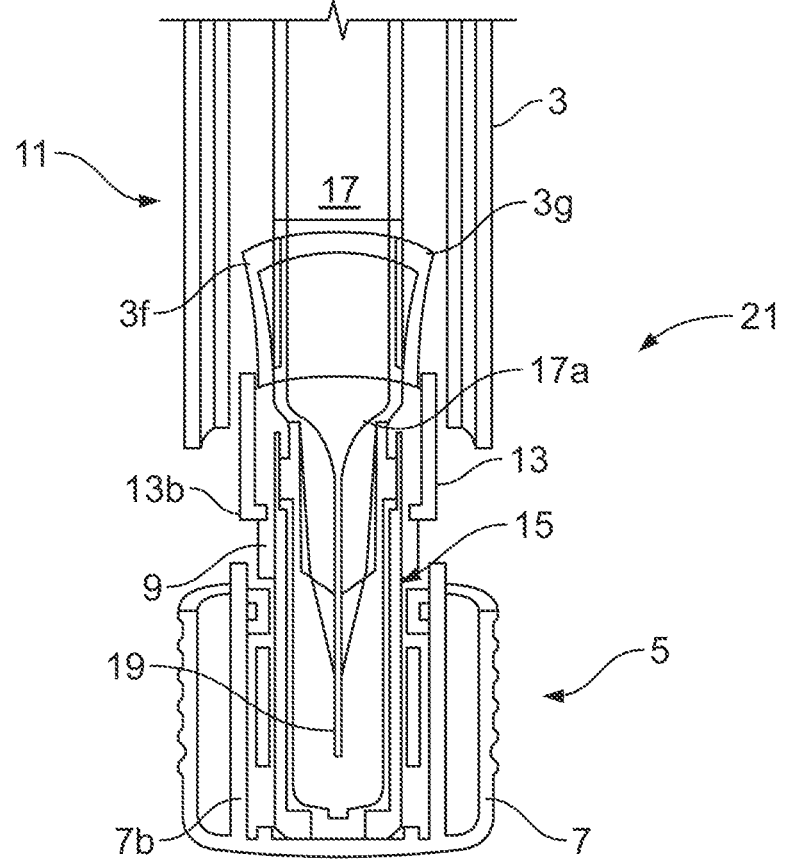
FIG. 12 shows a longitudinal section of a sub-assembly comprising the cap assembly and the medicament container assembly during assembly.

FIG. 12 shows a longitudinal section of an example of a sub-assembly. Sub-assembly 21 includes the cap assembly 5 and the medicament container assembly 11. FIG. 12 shows the sub-assembly 21 during assembly. The squeeze member 9 is in the first position inside the tubular body 7b of the cap 7, and the delivery member shield 15 is arranged in the channel of the squeeze member 9. The medicament container 17 has been arranged inside the body 3, and extends through the through-opening 3e of the tubular portion 3d, with a neck portion 17a of the medicament container 17 extending proximally beyond the tubular portion 3d. The delivery member 19 is arranged in the delivery member shield 15.

Figure 13:
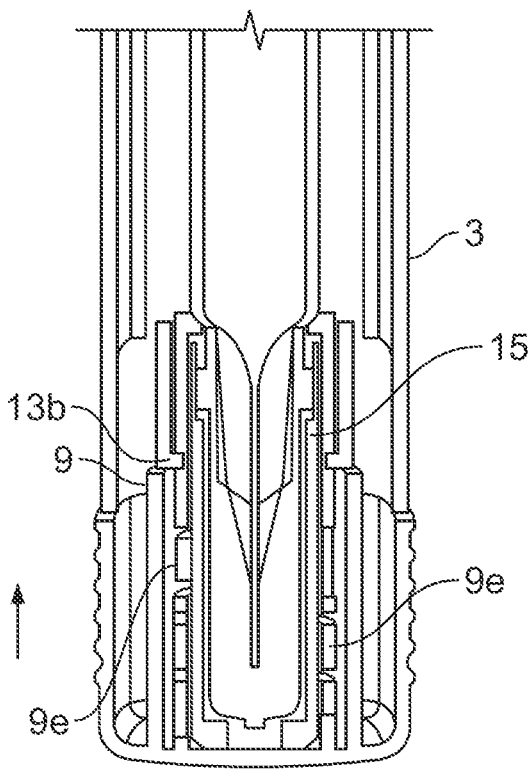
FIG. 13 shows a longitudinal section of the sub-assembly in FIG. 12 when the cap assembly and the medicament container assembly have been assembled.

In FIG. 13, the sub-assembly 21 is shown in an assembled state. The distal end face of the squeeze member 9 was pushed towards the proximal end flange 13*b* of the clamp member 13 as the cap assembly 5 and the medicament container assembly 11 were moved towards each other, causing the squeeze member 9 to move from the first position to the second position, and thereby rotate due to the cooperation between the cam structure 7*f* of the cap 7 and the proximal end face 9*a* of the squeeze member 9. The radial arms 9*e* of the squeeze member 9 have thus moved radially inwards as they were pressed towards the inner walls of the tubular body 7*b*, outside the radial recesses 7*d*, causing the radial arms 9*e* to engage with the delivery member shield 15.

Figure 14:
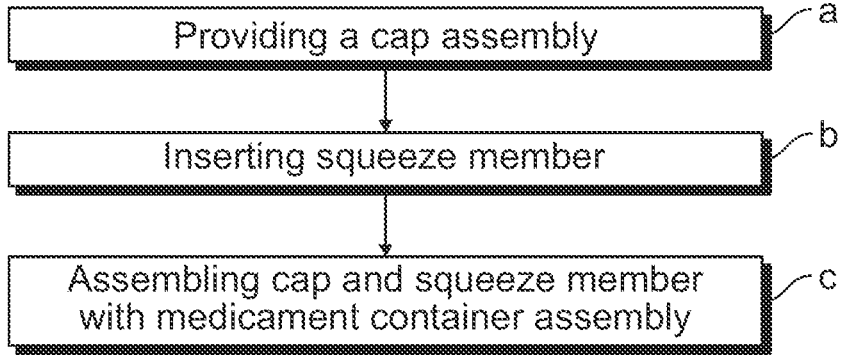
FIG. 14 is a flowchart showing a method of assembling a sub-assembly including the cap assembly and the medicament container assembly.

FIG. 14 shows a flowchart of a method of assembling a sub-assembly, for example sub-assembly 21.

In a step a) the cap assembly 5 is provided.

In a step b), the squeeze member 9 is inserted into the distal opening 7*c* of the tubular body 7*b* of the cap 7. The squeeze member 9 is moved towards the bottom structure 7*e* of the tubular body 7*b* until the proximal end face 9*a* of the squeeze member 9 contacts the bottom structure 7*e*, with each elevated portion 9*b* of the squeeze member 9 being arranged closer to an elevated portion 7*g* of the cam structure 7*f* than to the lowest elevational point of the corresponding cut-outs 7*h* of the cap 7. The squeeze member 9 is thus set in the first position.

In a step c) the cap 7 with the squeeze member 9 arranged therein is assembled with a medicament container assembly, for example medicament container assembly 11, including the medicament container 17 and the delivery member shield 15.

In examples where the cap assembly 5 is assembled with the medicament container assembly 11, the distal end of the squeeze member 9 is pushed against the proximal end flange 13*b* of the clamp member 13 provided around the support structure 3*c* of the body 3 and is moved in the distal direction, causing the squeeze member 9 to move in the proximal direction from the first positon to the second position. Hence, during the assembly in step c), the squeeze member 9 is pushed further into the cap 7, moving from the first position to the second position, causing the squeeze member 9 to rotate and grip the delivery member shield 15.

It should be noted that the cap assembly 5 could alternatively be assembled with another type of medicament container assembly, provided that the medicament container assembly has a support surface against which the distal end face of the squeeze member may be pushed during assembly, to move the squeeze member from the first position to the second position.

Figure 15:
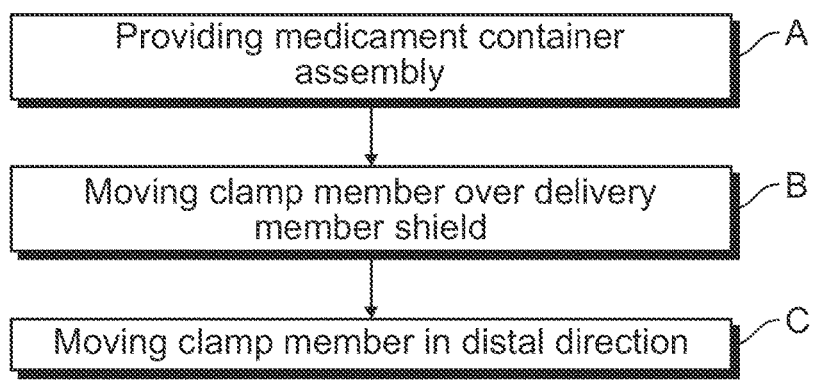
FIG. 15 is a flowchart showing a method of assembling a sub-assembly including the cap assembly and the medicament container assembly.

The medicament container assembly 11 may be assembled according to the method described by the flowchart in FIG. 15.

Hence, in a step A) the medicament container assembly 11 is provided.

In a step B) the medicament container 17 is inserted from a distal end opening of the body 3, with the delivery member 19 pointing in the proximal direction and the delivery member shield 15 being provided on the delivery member 19.

The medicament container 17 is moved in the proximal direction until the neck portion 17*a* of the medicament container 17 moves past the distal ends of the first gripper arm 3*f* and the second gripper arm 3*g*, and the delivery member shield 15 extends proximally through a proximal opening of the body 3.

In a step C) the clamp member 13 is moved over the delivery member shield 15, and into the body 3 through the proximal opening thereof.

In a step D) the clamp member 13 is moved in the distal direction over the tubular portion 3*d*, and thus over the first gripper arm 3*f* and the second gripper arm 3*g*. The first gripper arm 3*f* and the second gripper arm 3*f* are thereby bent or flexed radially inwards by the inner surface or wall of the clamp member 13.

In step D) the medicament container 17 may furthermore be pushed distally until the clamp member 13 reaches an end position, i.e. when the proximal end flange 13*b* bears against the proximal end of the tubular portion 3*d*, and the first gripper arm 3*f* and the second gripper arm 3*g* snap around the neck portion 17*a* of the medicament container 17, thereby providing support of the neck portion 17*a*.

In case that the cap assembly 5 is assembled with the exemplified medicament container assembly 11 the steps a)-c) and steps A)-D) are interconnected, in the sense that prior to step c) the medicament container assembly 11 has typically been assembled according to steps A-C, while step D) and step c) may be carried out simultaneously. Thus in step D) the clamp member 13 may be pushed distally by the squeeze member 9 and the medicament container 17 and delivery member shield 15 may be pushed distally by the cap 7, as the delivery member shield 15 is arranged in the squeeze member 9 and the cap 7 is moved distally towards the proximal end of the body 3.

Figure 16:
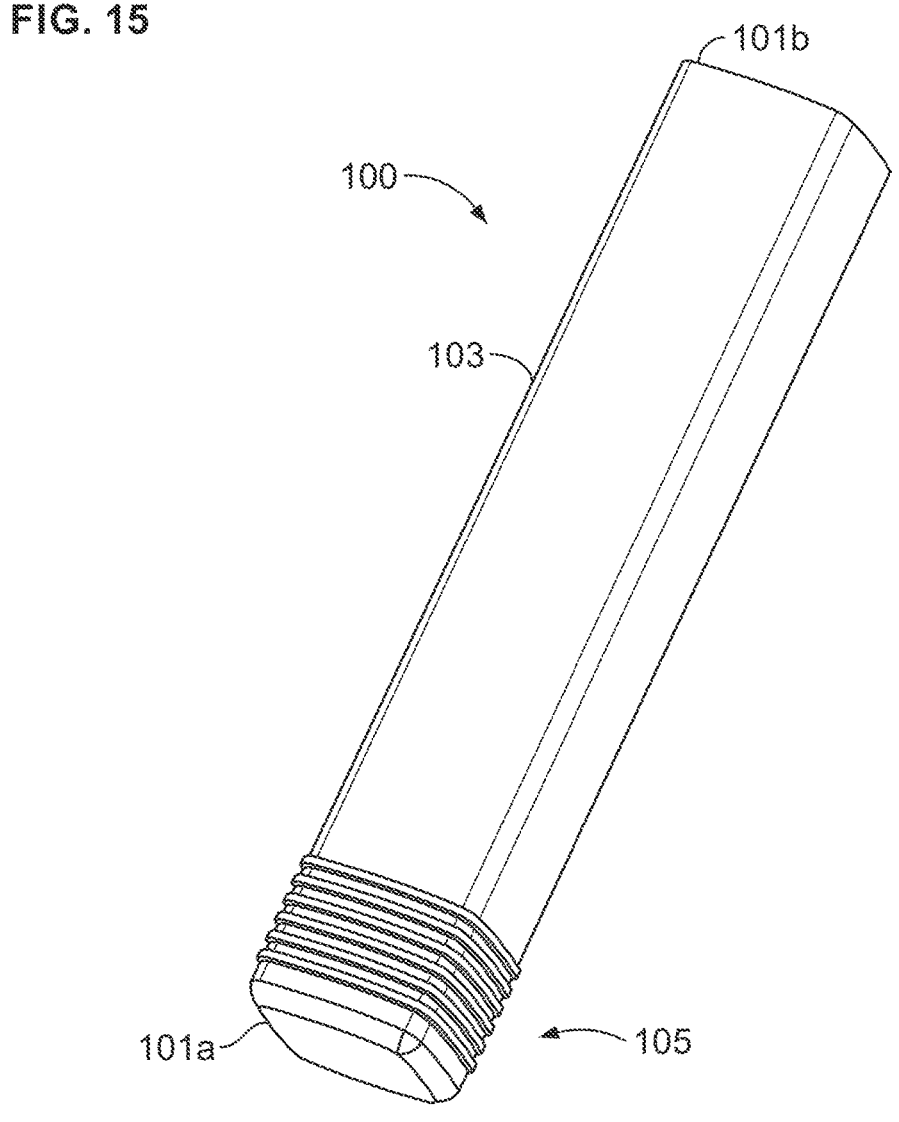
FIG. 16 illustrates a perspective view of an example medicament delivery device without an activation assembly, according to an example embodiment of the present disclosure.

With reference to FIGS. 16-28, another example of a cap assembly in accordance with the present disclosure will be described. FIG. 16 shows a perspective view of a medicament delivery device 100, which in the present case may also be seen as a sub-assembly of a medicament delivery device, because the depicted example does not comprise an activation assembly, which is to be mounted to a distal end of the medicament delivery device 100. The example medicament delivery device 100 shown in FIG. 16 has a proximal end 101*a* and a distal end 101*b*, and comprises a body, or housing, 103, and a cap assembly 105. An activation assembly (not shown) may be mounted to the distal end 101*b*.

Figure 17:
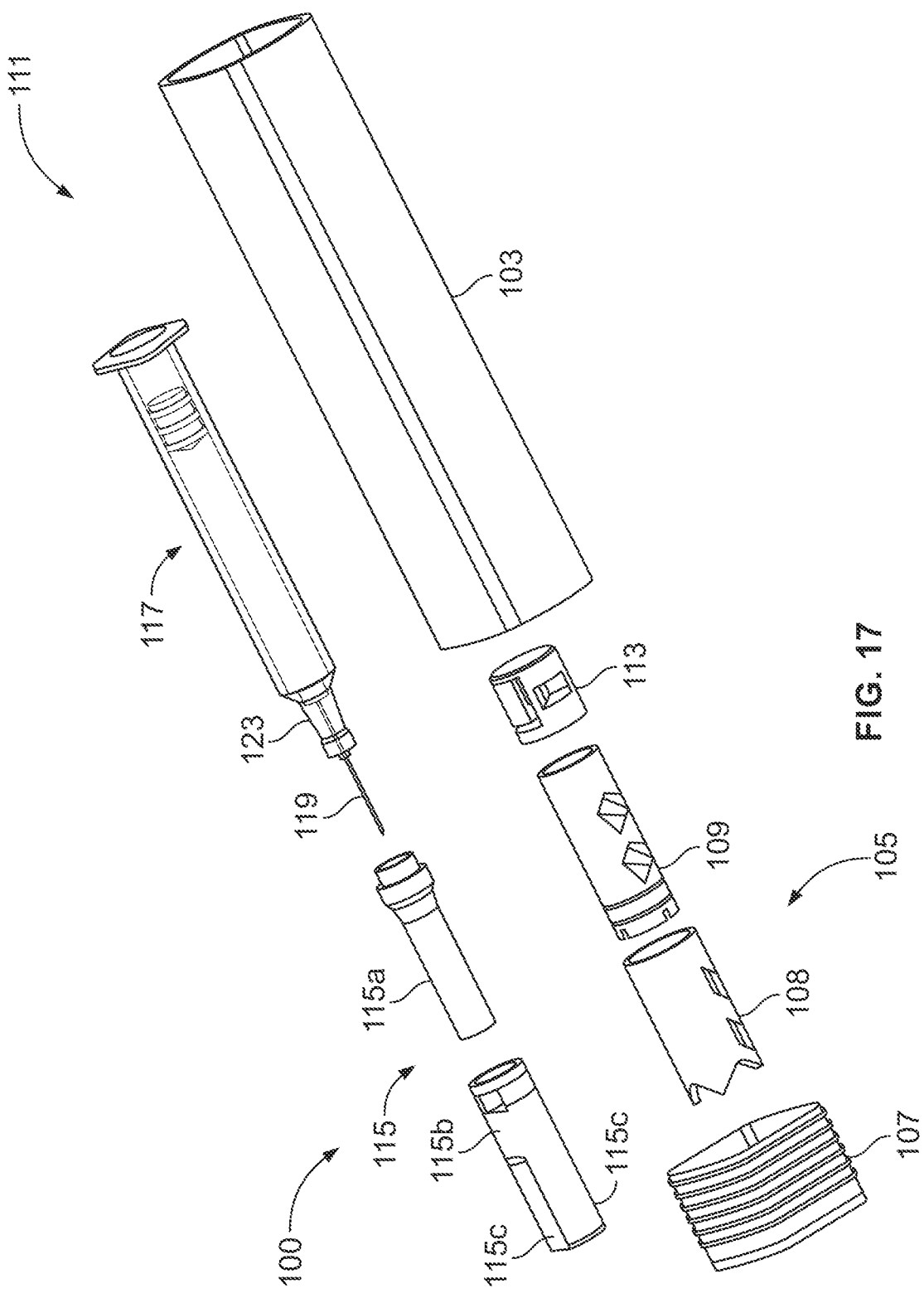
FIG. 17 illustrates an exploded view of the example medicament delivery device of FIG. 16, according to an example embodiment of the present disclosure.

Turning now to FIG. 17, an exploded view of the medicament delivery device 100 is shown. The medicament delivery device 100 comprises the cap assembly 105, which includes a cap 107, a spinner 108, a squeezer 109, and a clamp 113. The medicament delivery device 100 further includes a medicament container assembly 111 that includes body 103, a delivery member shield 115 and a medicament container 117 including a delivery member 119. According to the example shown in FIG. 17, the medicament container 117 is a syringe and the delivery member 119 is a needle. Moreover, the example delivery member shield 115 includes a flexible inner member 115*a* configured to receive the delivery member 119 and a rigid outer member 115*b* configured to receive the flexible inner member 115*a*. The rigid outer member 115*b* has chamfered outer surfaces 115*c* extending parallel with each other in the longitudinal direction of the delivery member shield 115. Although the example delivery member shield 115 is a rigid needle shield, in other example embodiments, the delivery member shield 115 is a flexible needle shield.

Figure 18:
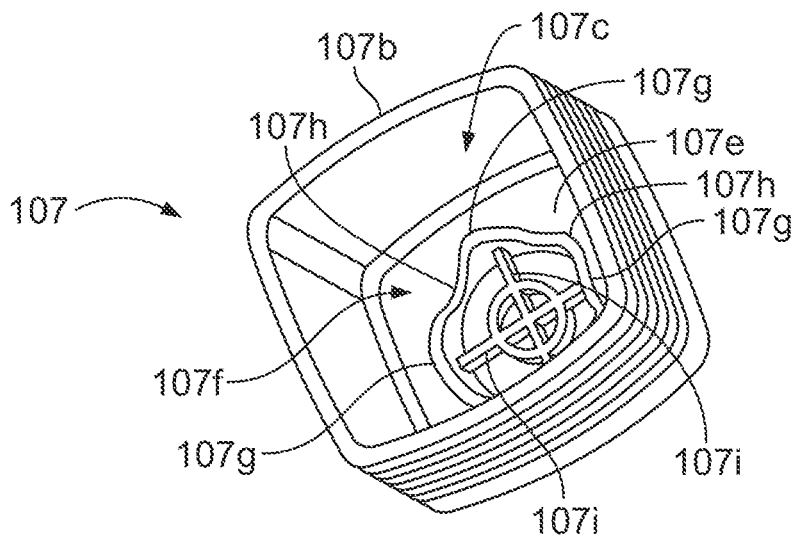
FIG. 18 illustrates a perspective view of an example cap of the example medicament delivery device of FIG. 16, according to an example embodiment of the present disclosure.

FIG. 18 shows a detailed view of the cap 107. The cap 107 is configured to be mounted to a proximal end of the medicament delivery device 100. The example cap 107 has a body 107*b* that has an axially extending distal opening 107*c*. The cap 107 is configured to receive the spinner 108 in the distal opening 107*c*. Further, the cap 107 has a proximal end 107*e*, and the proximal end 107*e* has a cam surface 107f. The cam surface 107f is configured to cooperate with a proximal end face of the spinner 108. According to the present example, the cam surface 107f is annular in a radial plane.

The cam surface 107f has a plurality of slanting surfaces, forming a gradually increasing and decreasing teeth-like structure in the circumferential direction. Hereto, the cam surface 107f has a plurality of elevated portions 107g and cut-outs 107h with oppositely arranged inclined surfaces. Between each pair of adjacent elevated portions 107g, there is provided a cut-out 107h. This configuration of the cam surface 107f allows for cooperation with the corresponding structure of the proximal end face of the spinner 108, as will be described in more detail in the following.

Figure 19:
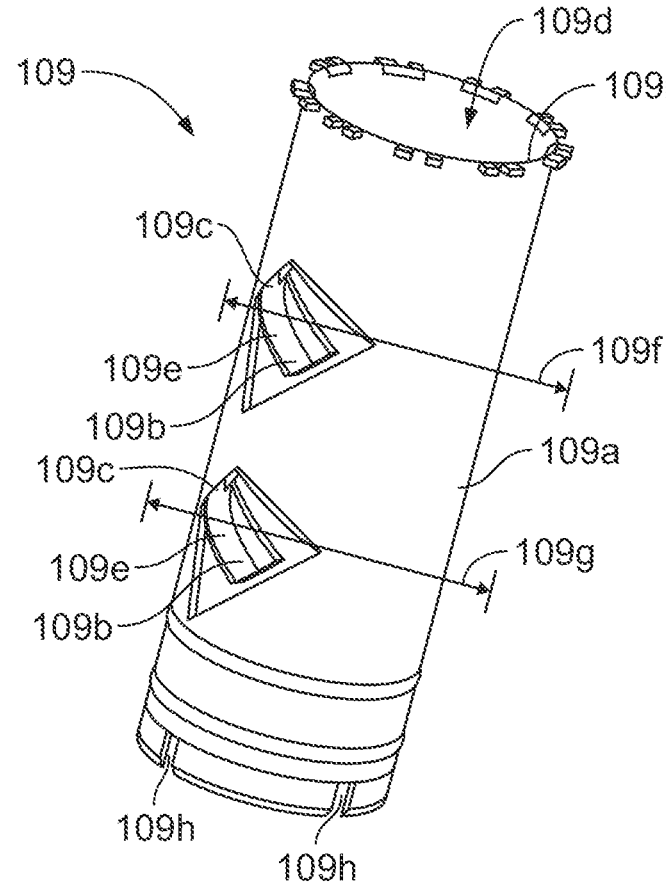
FIG. 19 illustrates a perspective view of an example squeezer of the example medicament delivery device of FIG. 16, according to an example embodiment of the present disclosure.

FIG. 19 illustrates a detailed view of the squeezer 109. The squeezer 109 is elongated and has a tubular shape. The squeezer 109 has a channel 109d extending in the longitudinal direction through the squeezer 109, and the channel 109d is configured to receive the delivery member shield 115.

The squeezer 109 comprises a plurality of radial arms 109e which are flexible in the radial direction. The radial arms 109e extend from the main body 109a of the squeezer 109 and have an increasing thickness towards their end portions 109b relative to the point of attachment 109c to the main body 109a of the squeezer 109. Hereto, the end thickness of each radial arm 109e is thicker than the thickness of the channel wall 109i of the main body 109a. In an example embodiment, the thickness of each radial arm 109e is at least 5% thicker than the thickness of the channel wall 109i. In another example, the thickness of each radial arm 109e is at least 10% thicker than the thickness of the channel wall 109i. Other example thicknesses are possible as well.

As seen in FIG. 19, the radial arms 109e form part of the channel wall 109i. The radial arms 109e are by default configured to flex radially outwards from the outer surface of the squeezer 109, as shown in FIG. 19. Hereto, the radial arms 109e protrude radially from the outer surface of the main body 109a of the squeezer 109 when no external force is applied to the radial arms 109e.

In an example embodiment, the squeezer 109 includes a plurality of sets of radial arms. For instance, as can be seen with reference to FIG. 19 in combination with FIG. 28, the squeezer 109 has (i) a plurality of arms 109e in a first radial plane 109f along the axial direction of the squeezer 109 and (ii) a plurality of radial arms 109e in a second plane 109g axially spaced apart from the first plane. The example squeezer 109 hence has several layers of radial arms 109e, in the axial direction of the squeezer 109. Although this example shows two layers of radial arms 109e, in other example embodiments, more or fewer layers of radial arms 19e are possible. Further, although in the example of FIG. 19 the radial arms 109e are angled with respect to the radial planes 109f and 109g, in other examples embodiments, the radial arms 109e are parallel or substantially parallel to the radial planes 109f and 109g.

Figure 20:
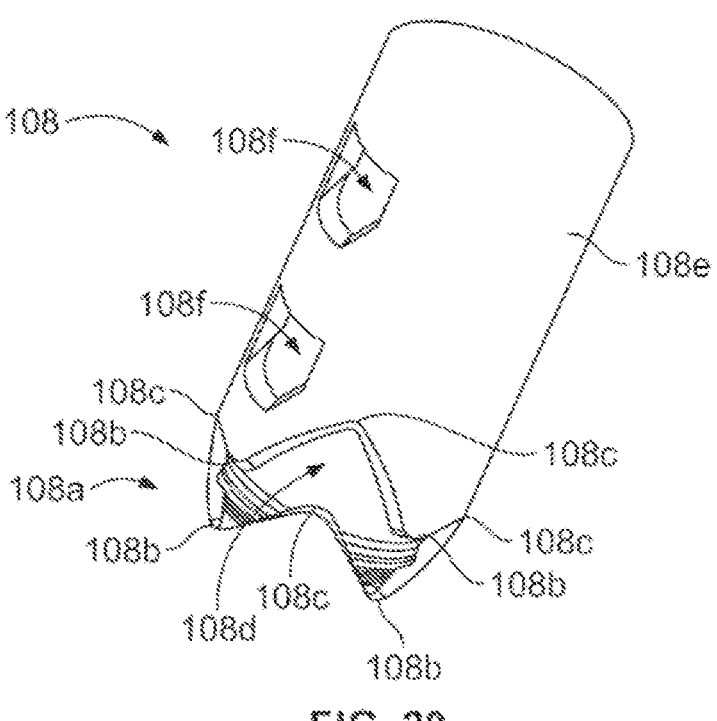
FIG. 20 illustrates a perspective view of an example spinner of the example medicament delivery device of FIG. 16, according to an example embodiment of the present disclosure.

FIG. 20 illustrates a detailed view of the spinner 108. In this example embodiment, the spinner 108 is elongated and has a tubular shape. The spinner 108 has a body 108e defining a longitudinally extending channel 108d configured to receive the squeezer 109. The spinner 108 furthermore has a proximal end face 108a configured to cooperate with the cam surface 107f of cap 107. In particular, the proximal end face 108a includes a plurality of elevated portions 108b. Between each pair of adjacent pair of elevated portions 108b is a cut-out 108c with oppositely inclined or sloping surfaces. The proximal end face 108a is hence provided with a plurality of teeth in the circumferential direction of the spinner 108, with a gradually increasing and decreasing elevation.

Figure 21:
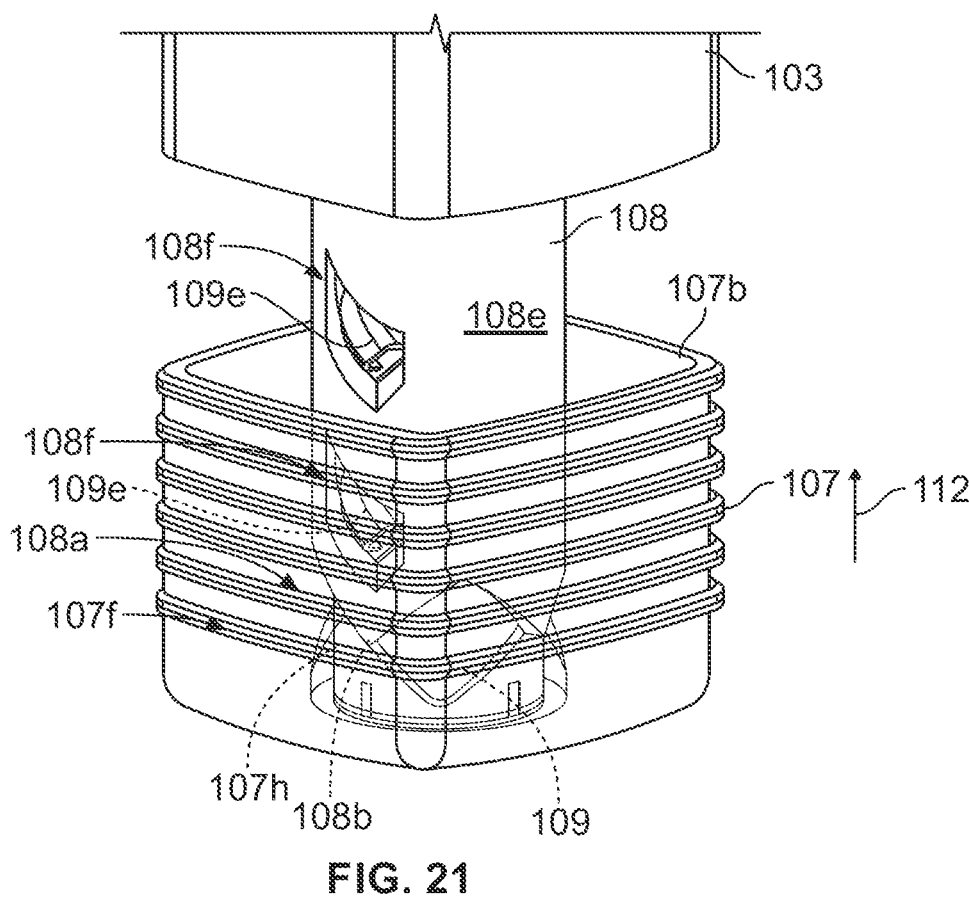
FIG. 21 illustrates a perspective view of a proximal end of the example medicament delivery device of FIG. 16 in an initial state, according to an example embodiment of the present disclosure.

The spinner 108 also includes a plurality of holes 108f in the body 108e that are configured to receive the plurality of radial arms 109e of the squeezer 109 when the squeezer 109 is inserted into the spinner 108. In particular, when the squeezer 109 is inserted into the channel 108d, the radial arms 109e may deflect radially inward so that the squeezer 109 is able to move through the channel 108d. Further, when the radial arms 109e align with the holes 108f, the radial arms 109e will flex outward into the holes 108f to return to their default position. This default position of the radial arms 109e is shown in FIGS. 19 and 21.

During an assembly process of the medicament delivery device 100, axial displacement of the spinner 108 from (i) a first position in which the proximal end face 108a bears against the cam surface 107f and each radial arm 109e of the plurality of radial arms is positioned in a respective hole 108f of the plurality of holes to (ii) a second position in which the spinner 108 is received further by the cap 107 causes rotation of the spinner 108 relative to the cap 107 and the squeezer 109. The rotation of the spinner 108 relative to the cap 107 and the squeezer 109 causes the body 108e of the spinner 108 to force each radial arm 109e out of the respective hole 108f and into the longitudinally extending channel 109d, so as to reduce a cross-sectional area of the longitudinally extending channel 109d. This reduction of the cross-sectional area of the longitudinally extending channel 109d allows the squeezer to securely grip or squeeze the delivery member shield 115.

The axial displacement from the first position to the second position during the assembly process is described in greater detail with reference to FIGS. 21-24. FIG. 21 shows the spinner 108 arranged inside the body 107b of the cap 107. The spinner 108 is arranged in the first position relative to the cap 107. Here, the proximal end face 108a of the spinner 108 bears against the cam surface 107f arranged inside the body 107b. Each elevated portion 108b of the spinner 108 bears against a respective top portion of the cut-out 107h, closer to an elevated portion of the cam surface 107f than to the lowest elevational point of the cut-out 107h. As shown in the top view of FIG. 23, when the spinner 108 is in this first position the radial arms 109e are not yet extending into the channel 109d. Rather, the radial arms 109e are in their default position and are received by holes 108f.

Figure 22:
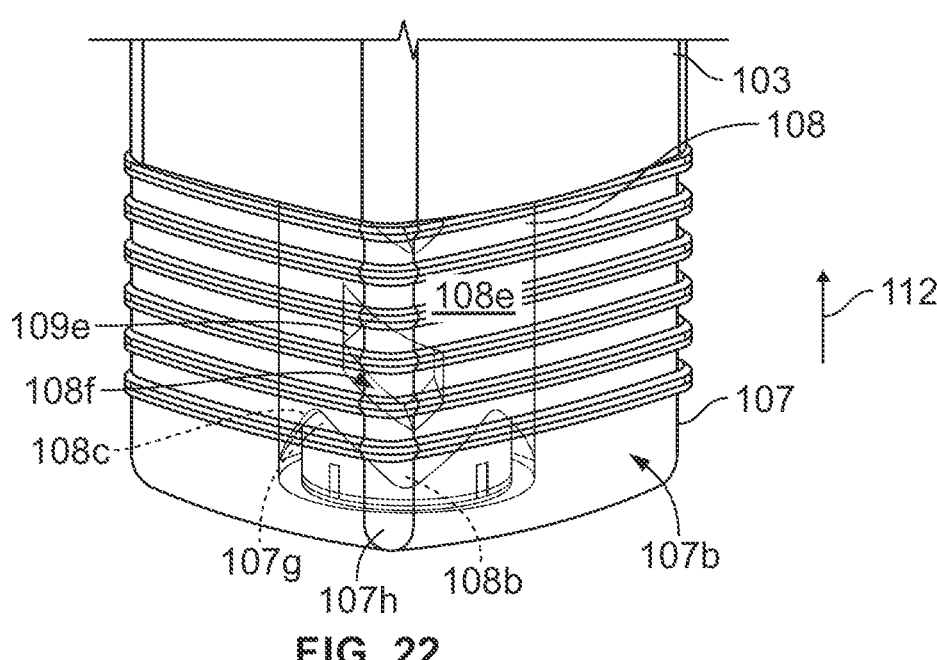
FIG. 22 illustrates a perspective view of a proximal end of the example medicament delivery device of FIG. 16 in an assembled state, according to an example embodiment of the present disclosure.
Figure 23:
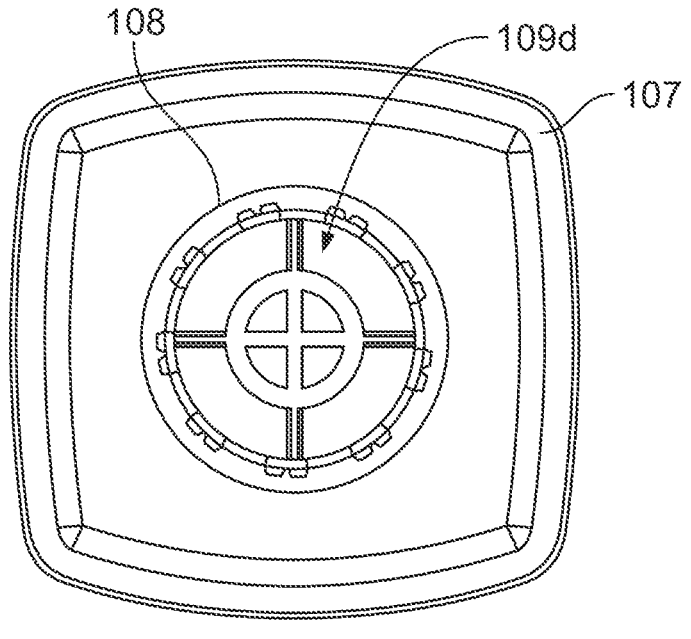
FIG. 23 illustrates a top view of a proximal end of the example medicament delivery device of FIG. 16 in an initial state, according to an example embodiment of the present disclosure.

FIG. 22 shows the spinner 108 in the second position. In the second position, the spinner 108 has been axially displaced relative to the first position shown in FIG. 21. In particular, the spinner 108 has been further received by the body 107b. In an example embodiment, this occurs as the cap 107 is moved in distal direction 112 toward body 103. Due to this proximal displacement of the spinner 108, the proximal end face 108a and the cam surface 107f have cooperated, causing the spinner 108 to rotate relative to the cap 107 and the squeezer 109. Hereto, the elevated portions 108b of the proximal end face 108a have slid down to the lowest elevational points of the cut-outs 107h of the cam surface 107f. Moreover, the elevated portions 107g of the cam surface 107f have been fully received by the cut-out 108c of the proximal end face 108a of the spinner 108.

This rotation of the spinner 108 relative to the cap 107 and the squeezer 109 causes the body 108e of the spinner 108 to force each radial arm 109e out of the respective hole and into the first longitudinally extending channel, so as to reduce a cross-sectional area of the first longitudinally extending channel. In an example embodiment, during this rotation of the spinner 108 from the first position to the second position, the spinner 108 moves axially relative to the squeezer 109.

In an example embodiment, the squeezer 109 is rotationally fixed to the cap 107. The squeezer 109 and the cap 107 may be rotationally fixed in any suitable manner. For instance, in the illustrated example, the cap 107 includes protrusions 107*i* (see FIG. 18) at the proximal end 107*e*, and the squeezer 109 includes recesses or slits 109*h* (see FIG. 19) at the proximal end of the squeezer 109. During the assembly process, the protrusions 107*i* may be positioned in the slits 109*h* so that the squeezer 109 and the cap 107 are rotationally fixed to one another.

Figure 24:
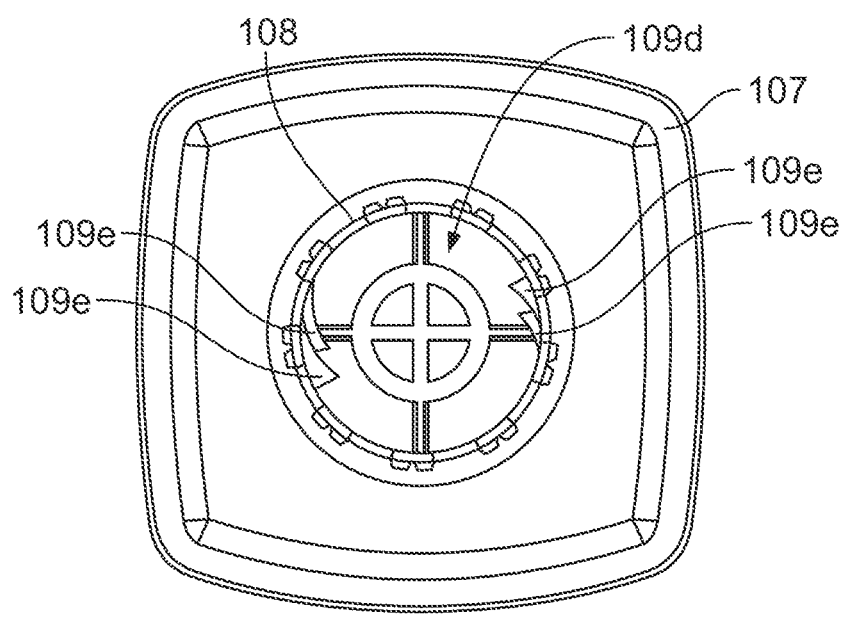
FIG. 24 illustrates a top view of a proximal end of the example medicament delivery device of FIG. 16 in an assembled state, according to an example embodiment of the present disclosure.

In FIG. 24, a top view of the situation shown in FIG. 22 is depicted. As the spinner 108 rotates, the holes 108*f* move relative to the radial arms 109*e* and the body 108*e* of the spinner 108 engages the radial arms 109*e*. This engagement forces the radial arms 109*e* to be pressed or flexed radially inwards. In the example shown, two radial arms 109*e* are arranged opposite to each other in radial plane 109*f* (see FIG. 19) of the squeezer, such that the two radial arms 109*e* move towards each other as the spinner 108 moves from the first position to the second position. Similarly, two radial arms 109*e* are arranged opposite to each other in radial plane 109*g* (see FIG. 19) of the squeezer, such that the two radial arms move towards each other as the spinner 108 moves from the first position to the second position. Although the radial arms 109*e* in each radial plane 109*f*, 109*g* are spaced apart by approximately 180 degrees, in other examples the radial arms 109*e* may be spaced apart by a different number of degrees. Further, although each radial plane includes two radial arms, each radial plane may include more or fewer radials arms.

As described above, the radial arms 109*e* have end portions 109*b* that are thicker than the wall 109*i* thickness of the channel 109*d*, and therefore, the radial arms 109*e* are pressed into the channel 109*d*, reducing the cross-sectional area of the channel 109*d*. When the delivery member shield 115 is arranged in the channel 109*d*, the radial arms 109*e* will engage with, or press against, the outer surface of the delivery member shield 115. This engagement or pressing against creates a tight fit around the delivery member shield 115.

In an example embodiment, the cap assembly 105 also includes a clamp 113 connected to the distal end of the squeezer 109. In particular, the clamp 113 is axially fixed to the distal end of the squeezer 109. The clamp may help to secure the medicament container 117 when the cap assembly 105 is assembled on the medicament container assembly 111. With reference to FIGS. 25-28, the clamp 113 includes a main body 113*a*. In this example, the main body 113*a* is a tubular body and is configured to surround the medicament container 117. The clamp 113 also includes a plurality of clamp arms 113*b* flexible in a radial direction.

Figures 25, 26:
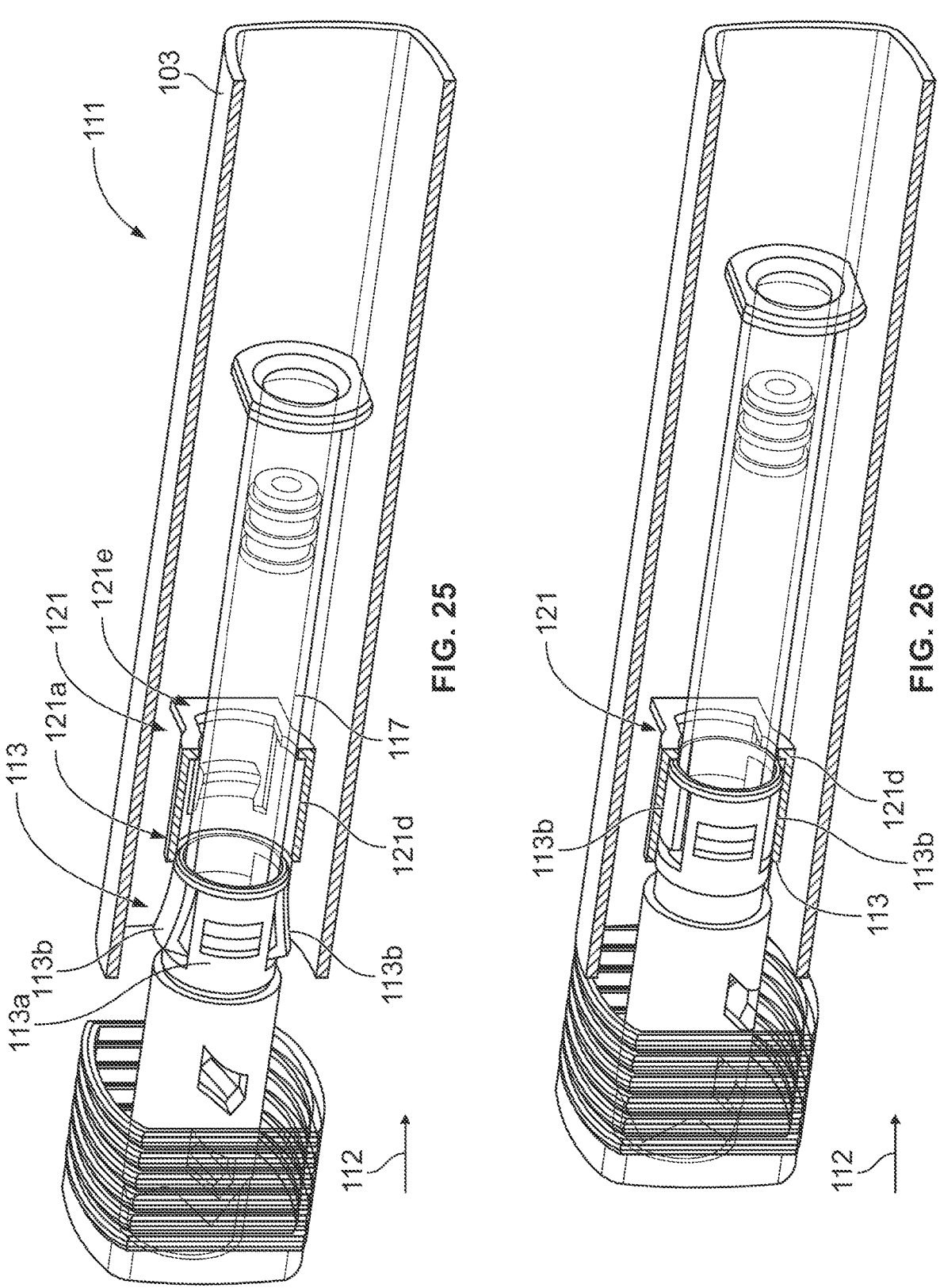
FIG. 25 illustrates a perspective and partial cross-sectional view of the example medicament delivery device of FIG. 16 in an initial state, according to an example embodiment of the present disclosure.
FIG. 26 illustrates a perspective and partial cross-sectional view of the example medicament delivery device of FIG. 16 in an assembled state, according to an example embodiment of the present disclosure.
Figure 28:
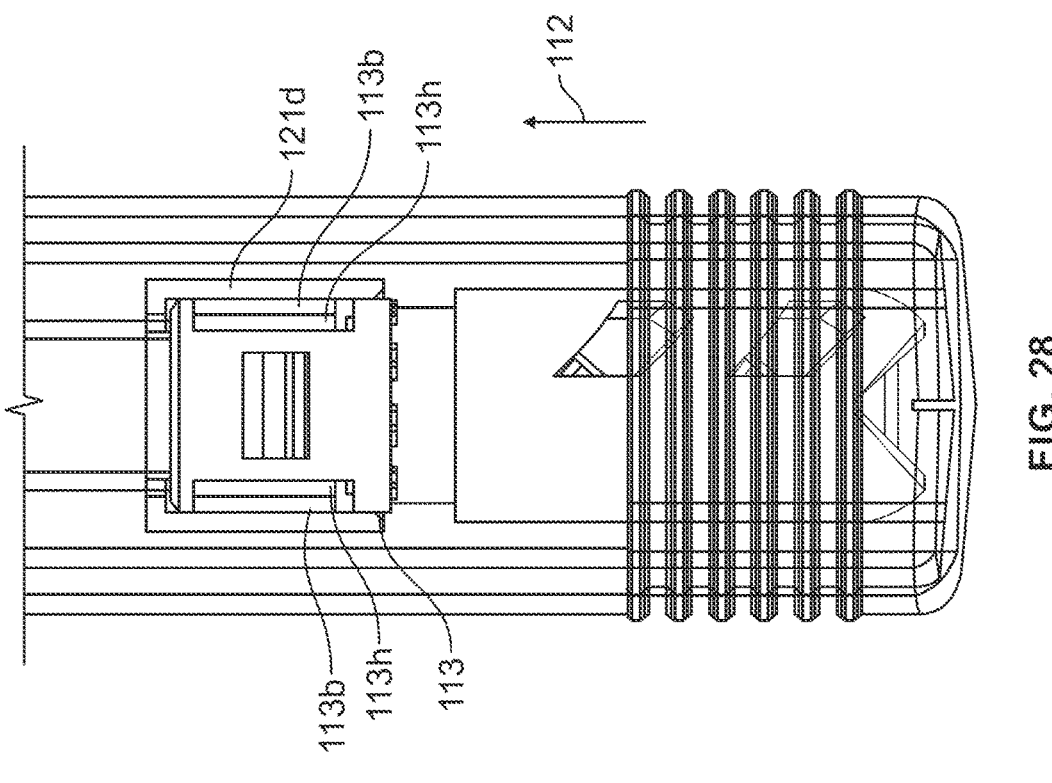
FIG. 28 illustrates a side view of a proximal end of the example medicament delivery device of FIG. 16 in an assembled state, according to an example embodiment of the present disclosure.
Figure 27:
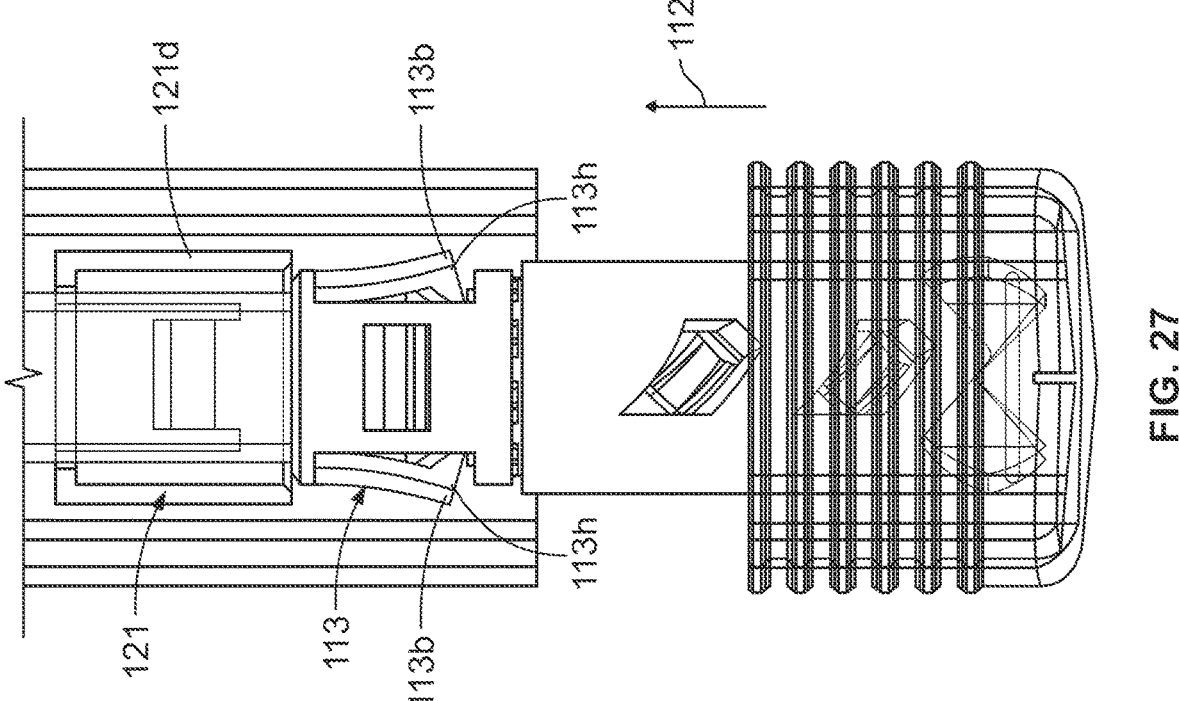
FIG. 27 illustrates a side view of a proximal end of the example medicament delivery device of FIG. 16 in an initial state, according to an example embodiment of the present disclosure.

The clamp 113 is configured to interact with the body 103 of the medicament container assembly 111 in order to secure the medicament container 117 when the cap assembly 105 is assembled on the medicament container assembly 111. In particular, the body 103 of the medicament container assembly 111 includes an inner seat 121 through which the medicament container 117 extends, and clamp 113 is configured to interact with this inner seat 121. As seen in FIG. 25, the inner seat 121 is a support structure having a main body 121*a* with a central tubular portion 121*d* provided with an axially extending through opening 121*e* configured to receive the medicament container 117. The central tubular portion 121*d* is also configured to receive the clamp 113 when the medicament container 117 is positioned in the inner seat 121.

During the assembly process, as cap 107 is moved in distal direction 112, the clamp 113 is inserted into the inner seat 121. When the clamp 113 is inserted into the inner seat 121, the clamp arms 113*b* move radially from an open position (see FIGS. 25 and 27) to a closed position (see FIGS. 26 and 28). The central tubular portion 121*d* forces the clamp arms 113*b* to flex inwards as the clamp 113 moves in the distal direction 112 into inner seat 121. When the clamp arms 113*b* are flexed inward to the closed position, the clamp arms 113*b* provide support of a neck 123 (see FIG. 17) of the medicament container 117. In particular, when the clamp 113 is in its end position during assembly (see FIG. 28), the gripper portion 113*h* (see FIGS. 27 and 28) of the clamp arms 113*b* bear against the neck 123 of the medicament container 117.

FIG. 29 illustrates an example method 200 of assembling a sub-assembly for a medicament delivery device. In an example embodiment, method 200 can be carried out in a sub-assembly in accordance with the present disclosure, such as the sub-assembly of medicament delivery device 100.

The method includes, at block 202, providing a cap assembly. In an example embodiment, the cap assembly is a cap assembly such as cap assembly 105. The method further includes, at block 204, inserting the squeezer 109 into the second longitudinally extending channel 108*d* of the spinner 108. In an example embodiment, inserting the squeezer 109 into the second longitudinally extending channel 108*d* of the spinner 108 involves inserting the squeezer 109 into the channel 108*d* until each radial arm 109*e* of the squeezer 109 is received by a respective hole 108*f* of the spinner 108.

Still further, the method includes, at block 206, inserting the spinner 108 into the cap 107 in a proximal direction and moving the spinner 108 until the proximal end face 108*a* of the spinner 108 contacts the cam surface 107*f* to obtain the first position of the spinner 108. The method also includes, at block 208, assembling the cap 107 with the spinner 108 and squeezer 109 arranged therein with a medicament container assembly 111 comprising a delivery member shield 115 and a syringe 117, such that the squeezer 109 grips the delivery member shield 115 and the clamp 113 grips a neck 123 of the syringe 117.

In an example embodiment of method 200 assembling the cap 107 with the spinner 108 and squeezer 109 arranged therein with the medicament container assembly 111 involves moving the spinner 108 axially relative to the cap 107, so as to cause the spinner 108 to move proximally inside the cap 107 from the first position to the second position. In another example embodiment of method 200, the medicament delivery device includes a body 103 surrounding the syringe 117 and comprising an inner seat 121 through which the syringe 117 extends. Further, assembling the cap 107 with the spinner 108 and squeezer 109 arranged therein with the medicament container assembly 111 involves inserting the clamp 113 into the inner seat 121 such that the clamp arms 113*b* move radially from the open position to the closed position, so as to provide support of a neck 123 of the syringe 117.

It should be understood that the illustrated components are intended as an example only. In other example embodiments, fewer components, additional components, and/or alternative components are possible as well. Further, it should be understood that the above described and shown embodiments of the present disclosure are to be regarded as non-limiting examples and that they can be modified within the scope of the claims.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

The invention claimed is:

1. An assembly for a medicament delivery device comprising:

a body having a longitudinal axis, a proximal end with an inner surface and a support structure comprising a tubular portion, where the support structure is axially fixed to the inner surface of the body; and a clamp slidably positioned relative to the tubular portion, where the clamp comprises a proximal end flange at its proximal end, and where the clamp has a first axial position, a second axial position, and an end position such that the end position is achieved during assemblage of the medicament delivery device, wherein when the clamp transitions from the first axial position to the second axial position, the clamp moves distally relative to the support structure and slidably engages around the tubular portion causing a flexible gripper arm on the support structure to flex radially inward, wherein the flexible gripper arm on the support structure continues to flex radially inward as the clamp transitions distally from the second axial position to the end position, and wherein the proximal end flange of the clamp bears against a proximal end of the tubular portion in the end position.

2. The assembly of claim 1, wherein the support structure further comprises an inner seat configured to accept a medicament container.

3. The assembly of claim 2, wherein an inside surface of the tubular portion has a diameter greater than an outside diameter of the clamp.

4. The assembly of claim 2, wherein the clamp is engaged with the medicament container when the clamp is in the second axial position.

5. The assembly of claim 2, wherein the flexible gripper arm comprises a gripper.

6. The assembly of claim 2, wherein when the clamp transitions from the first axial position to the second axial position, grippers engage a proximal portion of a syringe located within an inner seat of the proximal end of the body to secure the syringe from movement relative to the body.

7. The assembly of claim 1, wherein the flexible gripper arm has an open position and a closed position.

8. The assembly of claim 7, wherein the movement of the clamp from the first axial position to the second axial position causes the flexible gripper arm to transition from the open position to the closed position.

9. The assembly of claim 1, wherein both the clamp and the proximal end of the body are tubular shaped and the clamp is sized to fit within the proximal end.

10. An assembly for a medicament delivery device that secures a medicament container within the medicament delivery device, where the assembly comprises:

a body having a proximal end with an inner surface and a support structure comprising a tubular portion, where the support structure is axially fixed to the inner surface of the body;

an inner seat positioned within the tubular portion, where the inner seat is configured to accept a proximal end of a medicament container; and a clamp comprising two flexible arms in an exterior surface of the clamp, a proximal end flange at its proximal end, and a distal end having an outside diameter that is smaller than an inner diameter of the inner seat, where the clamp has a first axial position, and a second axial position, and an end position relative to the proximal end of the body such that the end position is achieved during assemblage of the medicament delivery device, wherein when the clamp moves distally the flexible arms slidably engage the inner seat causing the flexible arms to transition from an open position to a closed position, wherein the flexible arms remain in the closed position as the clamp moves distally from the second axial position to the end position, and wherein the proximal end flange of the clamp bears against a proximal end of the tubular portion in the end position.

11. The assembly of claim 10, wherein the flexible arms each comprises a gripper.

12. The assembly of claim 11, wherein the flexible arm engages an inner surface of the inner seat when the clamp moves from the first axial position to the second axial position and causes the grippers to move radially inward and engage a medicament container positioned within the inner seat.

13. The assembly of claim 10, wherein both the clamp and the inner seat are tubular shaped and the clamp is sized to fit within the inner seat.

14. A method of securing a medicament container within a medicament delivery device comprising:

providing a body having a proximal end with an inner surface and a support structure comprising a tubular portion, where the support structure is axially fixed to the inner surface of the body and comprises an inner seat, where a proximal portion of a syringe is positioned within the inner seat;

providing a clamp comprising a proximal end flange at its proximal end and a distal end having an outside diameter that is smaller than an inner diameter of the inner seat and comprising a flexible arm in an exterior surface of the clamp having a gripper;

moving the clamp axially and distally relative to both the inner seat and the syringe to cause the clamp to slidably engage an inner surface of the inner seat;

moving the flexible arm radially inward as the clamp engages the inner surface to cause the gripper to contact and secure the syringe within the body; and maintaining the flexible arm being moved radially inward as the clamp moves distally to an end position such that the end position is achieved during assemblage of the medicament delivery device, wherein the proximal end flange of the clamp bears against a proximal end of the tubular portion in the end position.

15. The method of claim 14, wherein axial movement of a cap assembly in a distal direction relative to the body causes the axial movement of the clamp.

16. The method of claim 15, wherein the cap assembly attaches to the body during the axial movement of the cap assembly such that the clamp is moved from a first axial position to a second axial position relative to the inner seat.

17. The method of claim 15, wherein the cap assembly comprises a squeezer that moves the clamp distally relative to the inner seat as the cap assembly is connected to the body.

\* \* \* \* \*